US006963398B2

(12) United States Patent
Sasaki et al.

(10) Patent No.: US 6,963,398 B2
(45) Date of Patent: Nov. 8, 2005

(54) LASER SCANNING MICROSCOPE

(75) Inventors: Hiroshi Sasaki, Tokyo (JP); Junichi Kitagawa, Fuchu (JP)

(73) Assignee: Olympus Optical Co., Ltd., Tokyo (JP)

( * ) Notice: Subject to any disclaimer, the term of this patent is extended or adjusted under 35 U.S.C. 154(b) by 274 days.

(21) Appl. No.: 10/262,596

(22) Filed: Oct. 1, 2002

(65) Prior Publication Data

US 2003/0107732 A1 Jun. 12, 2003

(30) Foreign Application Priority Data

Oct. 3, 2001 (JP) ........................................ 2001-307694

(51) Int. Cl.[7] .......................... G01J 3/30; G02B 21/00; G02B 21/06
(52) U.S. Cl. ........................ 356/318; 359/385; 359/368; 250/462.1
(58) Field of Search .......................... 356/318; 250/234, 250/206, 462.1, 458.1; 359/368, 385, 386, 389, 308, 739

(56) References Cited

U.S. PATENT DOCUMENTS

| 5,377,003 A | | 12/1994 | Lewis et al. | |
| 5,528,368 A | | 6/1996 | Lewis et al. | |
| 5,784,162 A | * | 7/1998 | Cabib et al. | 356/456 |
| 5,841,577 A | | 11/1998 | Wachman et al. | |
| 6,167,173 A | * | 12/2000 | Schoeppe et al. | 385/33 |
| 6,433,929 B1 | * | 8/2002 | Sasaki | 359/388 |
| 6,525,812 B1 | * | 2/2003 | Hartmann et al. | 356/318 |
| 6,686,583 B2 | * | 2/2004 | Engelhardt | 250/216 |
| 6,717,723 B2 | * | 4/2004 | Arai | 359/368 |

FOREIGN PATENT DOCUMENTS

| JP | 2000-056244 A | 2/2000 |
| JP | 2001-124997 A | 5/2001 |
| WO | WO 99/42884 A1 | 8/1999 |

* cited by examiner

*Primary Examiner*—Layla G. Lauchman
(74) *Attorney, Agent, or Firm*—Frishauf, Holtz, Goodman & Chick, P.C.

(57) ABSTRACT

The laser scanning microscope comprises an objective focusing a laser beam on a sample, and takes fluorescence or reflected light from the sample, optical scanning means for scanning the laser beam on the sample two-dimensionally, an acousto-optic device, arranged on an optical path of a fluorescence or a reflected light, which selects and deflects only a light beam with the wavelength which corresponds to incident fluorescence or the reflected light and a frequency of the applied high frequency voltage, optical detection means for detecting a light beam through the acousto-optic device, and frequency scanning means for switching and setting a frequency of a high frequency voltage applied to the acousto-optic device.

91 Claims, 6 Drawing Sheets

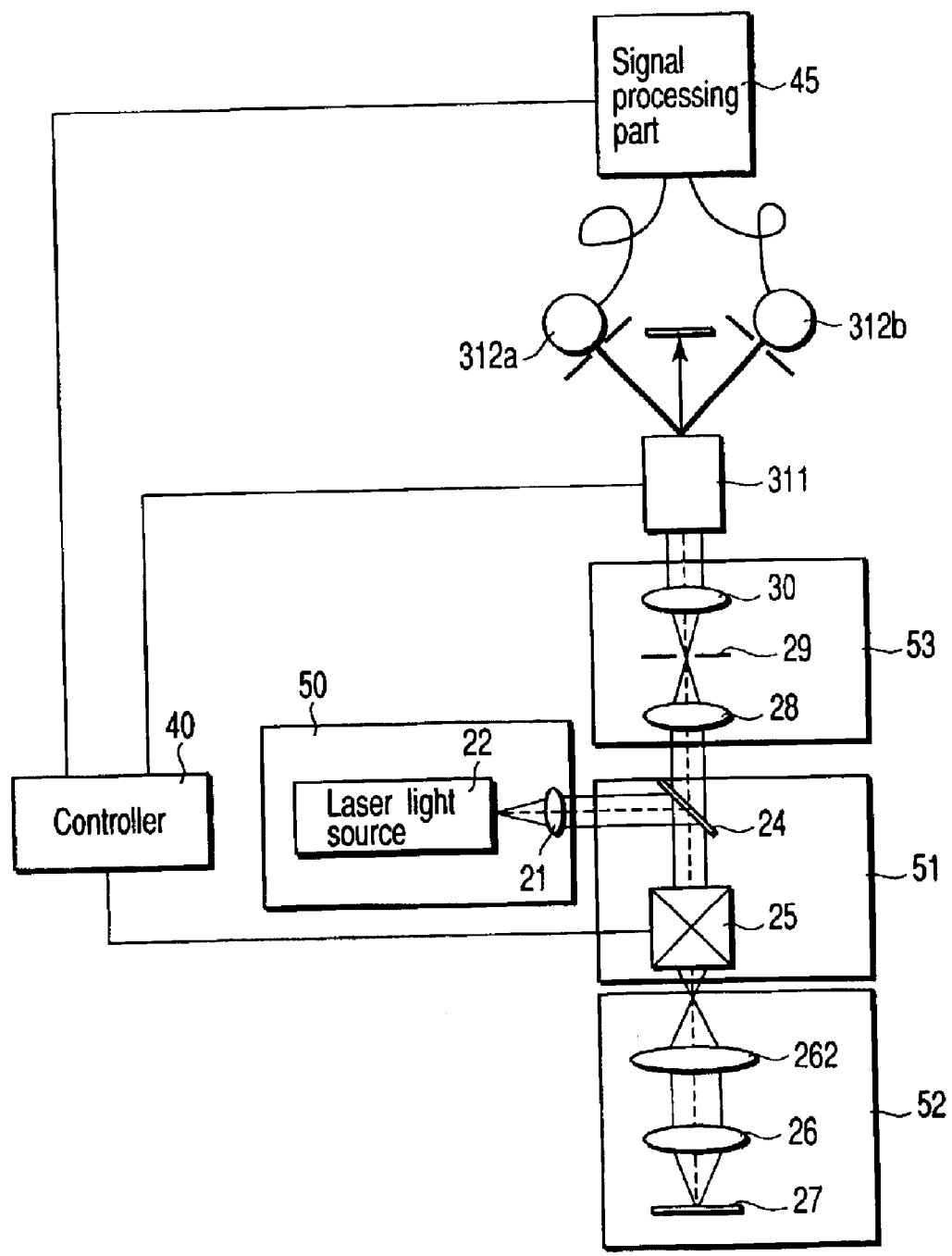
F I G. 4

LASER SCANNING MICROSCOPE

CROSS REFERENCE TO RELATED APPLICATIONS

This application is based upon and claims the benefit of priority from the prior Japanese Patent Application No. 2001-307694, filed Oct. 3, 2001, the entire contents of which are incorporated herein by reference.

BACKGROUND OF THE INVENTION

1. Field of the Invention

The present invention relates to a laser scanning microscope which can detect, for instance, a spectrum data of the fluorescence and reflected light at high speed.

2. Description of the Background Art

It is hoped to measure variety of detection factors with an increase in the lineup of a fluorescent reagent and the change in the labeled state in recent years. As the variety of detection factors, it is hoped to efficiently detect the spectrum and the deflection characteristic of the fluorescence and the measure quantity as the acquisition data in addition to fluorescent intensity. Furthermore, the downsizing as the device is expected.

A laser scanning microscope using an acousto-optic device (Acousto-Optic Tunable Filter: hereinafter, it is called an "AOTF" in the specification) is known (Japanese Patent Application KOKAI Publication No. 2001-124997).

In the laser scanning microscope, an optical element is connected at the next or later stage of a spectrum selective component (AOTF). And then, the excitation light can be selected by incidence of the laser beam from the first-order diffraction light beam optical path of the AOTF. As a result, the AOTF carries out a function of the beam splitter with high efficiency to lead the fluorescence from the microscope to the detector on the 0-th order diffracted light beam optical path. In addition, there is the following description in the Japanese Patent Application KOKAI Publication No. 2001-124997. It is possible to separate fluorescence to, for instance, two different polarized components by using decentralization or birefingent characteristics of the AOTF. The polarized laser scanning microscope which does not need a polarizer and an analyzer can be provided by detecting each component of these two polarized components.

However, in the combination of the AOTF and an optical element by the Japanese Patent Application KOKAI Publication No. 2001-124997, a wavelength which is matched to the excitation wavelength of the laser can be selected, but the spectroscopic effect which becomes a wavelength selection of the fluorescence is not achieved. Moreover, though the separation of the polarized component is achieved by using the birefingent of the prism of the AOTF statically, the acousto-optic effect of which the AOTF has is not positively used. Therefore, the polarized component of the fluorescence cannot be detected by the Japanese Patent Application KOKAI Publication No. 2001-124997, while selecting the wavelength (that is, while performing spectrum).

Therefore, since it becomes necessary to arrange the spectrometer such as a multiband detector, the grating spectrometer, and the prism spectrometer, etc. at further next or later stage of the AOTF and the optical element to select the wavelength by the Japanese Patent Application KOKAI Publication No. 2001-124997, enlargement of the device cannot be avoided.

The microscope which uses the AOTF is known (see U.S. Pat. No. 5,841,577).

In this microscope, the AOTF is arranged in the illumination optical path. And, the excitation light can be efficiently illuminated to the sample by overlapping two outgoing light beams, that the polarized components are different mutually again, of the wavelength selection with the AOTF by using synthetic means and being used as one excitation light. Moreover, by arranging the AOTF to the observation side, fluorescence whose wavelength is selected with the AOTF, from the sample can be observed with the CCD camera. Furthermore, U.S. Pat. No. 5,841,577 discloses a method of overlapping light having the separated different polarized components as an optical path again by using two AOTFs and a method of performing the incident fluorescence illumination by using the dichroic mirror.

However, U.S. Pat. No. 5,841,577 relates to a method of illuminating a fluorescent observation, and does not have a configuration for acquiring the spectrum data by selecting the wavelength with the laser scanning microscope. Though a fluorescent observation can be performed with the CCD camera by providing the AOTF in the observation optical path, there is a problem that an optical loss by detecting only one polarized component included in a first-order diffracted light beam and fluorescent intensity of an actual sample by this cannot be correctly reflected when applying to laser scanning microscope.

In addition, in U.S. Pat. No. 5,841,577 to block the 0-th order diffracted light beam which is not desired, the configuration of the device enlarges inevitably because it is necessary to use a condenser lens for the dark-field or the optical element which becomes a stopper on an optical axis and a synthetic means to overlap two separated optical path again as one excitation light.

BRIEF SUMMARY OF THE INVENTION

The laser scanning microscope according to one aspect of the present invention is characterized by comprising: an objective focusing a laser beam on a sample, and takes fluorescence or reflected light from the sample; optical scanning means for scanning the laser beam on the sample two-dimensionally; an acousto-optic device, arranged on an optical path of a fluorescence or a reflected light, which selects and deflects only a light beam with the wavelength which corresponds to incident fluorescence or the reflected light and a frequency of the applied high frequency voltage; optical detection means for detecting a light beam through the acousto-optic device; and frequency scanning means for switching and setting a frequency of a high frequency voltage applied to the acousto-optic device.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is a figure which shows a schematic configuration of the laser scanning microscope according to the third embodiment;

DETAILED DESCRIPTION OF THE INVENTION

Figure 1:
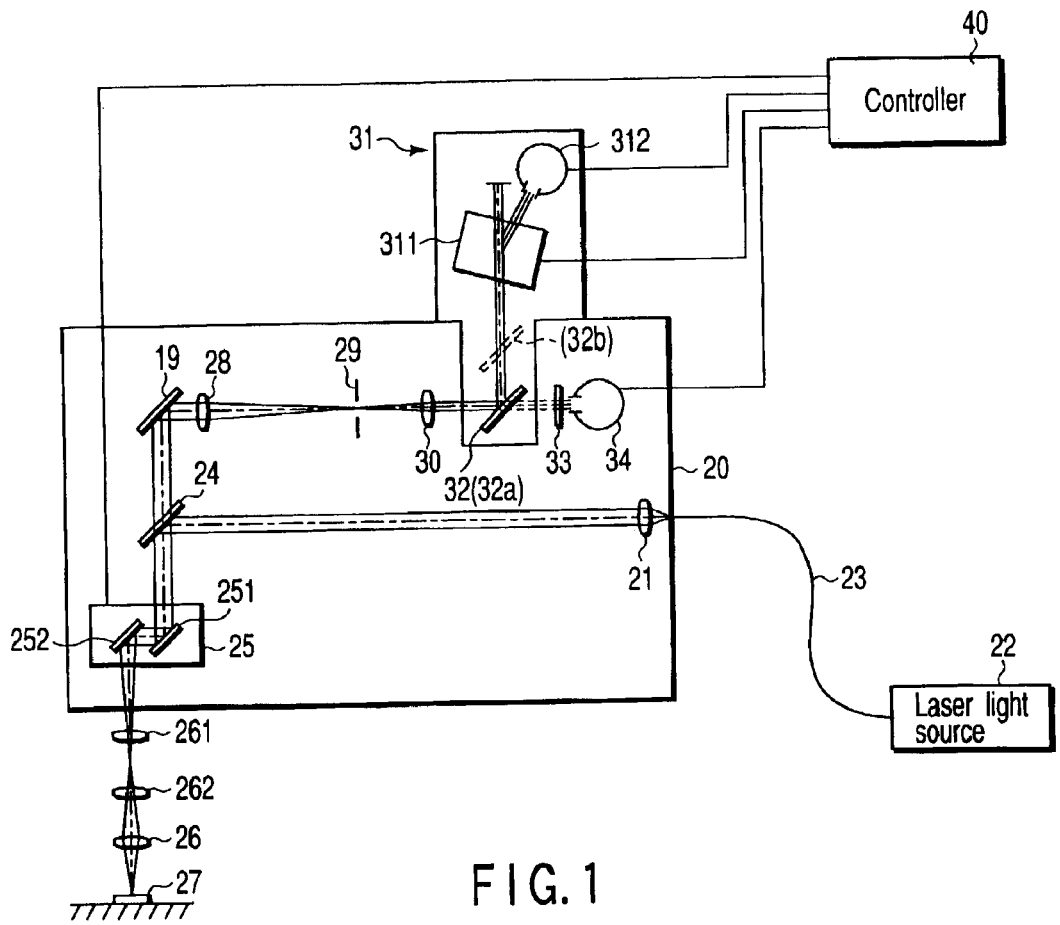
FIG. 1 is a figure which shows a main part configuration of the laser scanning microscope according to the first embodiment of present invention.

Hereinafter, embodiments of the present invention will be explained in detail referring to the drawings.

(First Embodiment)

FIG. 1 is a figure which shows a main part of the microscope according to the first embodiment of present invention. In FIG. 1, the collimator lens 21 is provided to the scanning unit 20. The laser beam emitted from the laser light source 22 is led to the collimator lens 21 through the optical fiber 23. The laser beam led to the scanning unit 20 is converted into a parallel light beam by the collimator lens 21, and led to the reflection optical path after the beam splitter 24. FIG. 1 shows a basic configuration of the system. Therefore, to give a plurality of the wavelengths to the laser light source 22, the laser may be the multi-line type, and may be configured by using a plurality of laser light sources and have a plurality of the dichroic mirrors 24.

Here, it is assumed that the wavelength of the laser beam emitted from the laser light source 22 is 488 nm of the Ar laser and the wavelength characteristics of the beam splitter 24 is to reflect the light with the wavelength of 488 nm, and to transmit the light with longer wavelength (500 nm to 700 nm) than 488 nm. The laser beam of 488 nm in wavelength reflected by the beam splitter 24 is deflected by the optical scanning mirrors 251 and 252 which are the galvanometer mirrors configuring the optical scanning means 25. The laser beam deflected by the optical scanning mirror 252 is focused and illuminated on the sample 27 by the objective 26 further through the tube lens 262 of the microscope and the pupil projection lens 261.

The optical scanning mirrors 251 and 252 control the scanning of the laser beam such that the laser beam is deflected along mutually orthogonal directions, and scans the focused optical spot on the sample 27 two-dimensionally. And, the fluorescence with longer wavelength than 488 nm generated from the sample by illuminating the laser beam of 488 nm travels in the same optical path of the laser beam and of the opposite direction (that is, the objective 26, the tube lens 262, and pupil projection lens 261), is reflected by the optical scanning mirrors 252 and 251, and is led to the penetration optical path of the beam splitter 24.

The fluorescence led to the penetration optical path of the beam splitter 24 is reflected with the reflection mirror 19, and thereafter is focused again by the confocal lens 28 on the confocal pinhole 29. The fluorescence transmitted through the confocal pinhole 29 is converted into the parallel light beam by the lens 30. The acousto-optic device unit 31 which configures the frequency scanning means is set on the optical path of the parallel light beam by the optical path switching mirror 32.

The optical path switching mirror 32 is set at the position 32b shown by the broken line in the figure and also can be mared away from the position 32a on the optical path of the parallel light beam. In a case that the optical path switching mirror 32 is saved at the position 32b, the fluorescence led to the corresponding optical path directly goes for optical detector 34 which has the photomultiplier tube through the barrier filter 33 which transmitted through the light in the fluorescent wavelength band and cuts the wavelength of the laser (488 nm here) and an optical amount thereof is detected.

The optical detector 34 is a detector to acquire the scanning image of the usual laser scanning microscope. The optical detector 34 detects a fluorescent optical amount of fluorescence corresponding to one optical spot one by one synchronizing with the scanning of the optical scanning mirrors 251 and 252. And, a two-dimensional image is obtained by displaying an optical amount at the optical of each spot position on each pixel of the monitor which is not shown in the figure. The two-dimensional image obtained here is an image which shows the sum total of an optical amount within the range of the wavelength extracted with the barrier filter 33 among the fluorescences emitted from the each optical spot position, and does not contain the detailed wavelength information on the spectrum characteristic data etc.

For instance, the acousto-optic device unit 31 is configured with the optical detector 312 (photomultiplier tube) for the acousto-optic device 311 (Hereafter, called an "AOTF") and the spectrum characteristic measurement as the optical detection means. The AOTF 311 has the crystal and the RF transducer not shown in the figure, usually. When the high frequency voltage (RF) of the desired frequency is applied to the RF transducer, the acoustic wave of the desired frequency is generated within the crystal. Only the wavelength which satisfies the condition of the Bragg reflection between the RF frequency and the wavelength of the incident light as a first-order diffracted light beam, and is detected with the optical detector 312. A device, which can perform photoelectric conversion and detect the signal, of other equal effects except PMT may be used as the detector 312.

The wavelength width of the deflected light as a first-order diffracted light beam by the one RF frequency is usually 3 nm or less, and the other wavelength light transmitted through the crystal of the AOTF 311 is guided to the optical path. Then, by switching or scanning the RF frequency one by one and measuring the optical amount of each frequency detected with the optical detector 312, it becomes possible to detect a spectrum characteristics of the fluorescence.

Here, the control part 40 shown in FIG. 1 controls the optical scanning mirrors 251 and 252, the optical detector 34, the optical detector 312, and the RF transducer based on instruction information (not shown in the figure). The control part 40 has the following three main functions.

(1) A function to match (synchronize) to the scanning timing of the optical scanning mirrors 251 and 252, and detect an incident optical amount to the optical detector 34 and the optical detector 312.

(2) A function to match (synchronize) to the scanning timing of the RF frequency and detect an optical amount of the optical detector 34 and the optical detector 312.

(3) A function to match (synchronize) to the scanning timing of the optical scanning mirrors 251 and 252, and scan the RF frequency, and to match (synchronize) to the scanning timing of the RF frequency and detect an optical amount of the optical detector 34 and the optical detector 312.

In the above-mentioned configuration, the operation to measure the spectrum characteristic data with the acousto-optic device unit 31 will be explained. First of all, when the acousto-optic device unit 31 is used, the optical path switching mirror 32 is moved to the position 32a with the switching mechanism not shown in the figure. As a result, the laser beam emitted from the laser light source 22 is deflected by the optical scanning mirrors 251 and 252. As a result, when an optical spot is focused at one arbitrary point on the sample 27, the fluorescence generated from the sample 27 transmitted through the confocal pinhole 29 through the beam splitter 24 etc. And, the fluorescence after the confocal spot 29 is converted into the parallel light beam with the lens 30, is reflected with the optical path switching mirror 32, and is an incident beam to the AOTF 311.

Here, the relationship of the RF frequency to the wavelength which satisfies the requirement of the Bragg reflection is as follows. It is assumed that the RF frequency decreases by 1 MHz when the wavelength lengthen at 4 nm such as 132 MHz at 492 nm, 131 MHz at 496 nm, 130 MHz at 500 nm, ... , 92 MHz at 652 nm, 91 MHz at 656 nm, 90 MHz at 660 nm. Though the relationship between the frequency and the RF wavelength actually might become non-linear relationship by the refraction index difference by the wavelength of the crystal of the AOTF 311, here, it will be explained as a linear relationship for the simplification.

If the frequency of 132 MHz of RF is applied to the crystal by the RF transducer in the AOTF 311, the light of the wavelength of 492 nm corresponding to this frequency is deflected as a first-order diffracted light beam. As a result, the intensity of the light of the wavelength in the vicinity of 492 nm is detected with the optical detector 312. If the RF frequency of 131 MHz corresponding to the frequency of 496 nm is applied to the crystal, the light of the wavelength of 496 nm is deflected as a first-order diffracted light beam. As a result, the intensity of the wavelength in the vicinity of 496 nm is detected with the optical detector 312.

Figure 2:
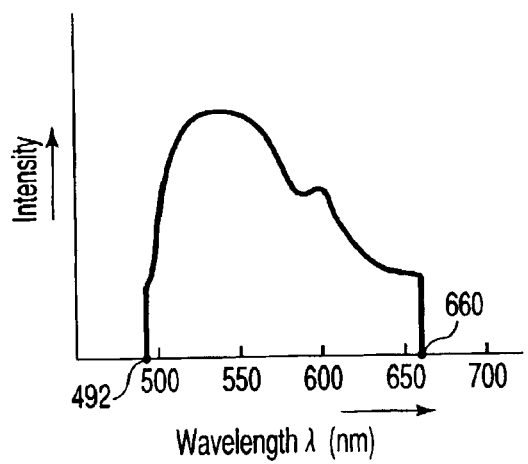
FIG. 2 is characteristic diagram which shows an example of the spectrum characteristic data acquired in FIG. 1.

Similarly, the intensity of the light of the wavelength corresponding to each frequency is detected with the optical detector 312 by switching (scanning) to 90 MHz corresponding to the RF frequency of 660 nm one by one for every 1 MHz. The spectrum characteristic data of the fluorescence from 492 nm to 660 nm is acquired as shown in FIG. 2 according to the above-mentioned process. The spectrum characteristic data obtained here is data of the fluorescence generated from one point on the sample to which an optical spot is formed.

In a case that the spectrum characteristic data from the wide range (range of the scanning image acquisition) of the sample is obtained, the above-mentioned process of obtaining the spectrum characteristic data of the fluorescence from one optical spot on the sample 27 (optical amount measurement of the wavelength corresponding to each RF frequency by the scanning of the RF frequency and the optical detector 312) while scanning the optical scanning mirrors 251 and 252 and scanning the optical spot is performed. In this case, the control part 40 controls the frequency scanning with the optical scanning mirrors 251 and 252 and the RF transducer and the measurement of light optical detectors 312 by synchronizing them.

Here, the acquisition time of the spectrum characteristic data of each pixel will be considered. For instance, the detection time in an optical detector of one wavelength corresponding to the one RF frequency is assumed to be one microsecond by the image of 512×512 pixels, and the switching time of the RF frequency is assumed to be one microsecond. The time of data acquisition in one pixel becomes (132−90) ×2+1=85 microseconds since the RF frequency is switched every 1 MHz from 132 MHz to 90 MHz, thereby the time of data acquisition in all pixels becomes 85 ($\mu$sec) ×512×512=22.3 sec. Data is acquired within 30 seconds even if the allowance of the optical scanning mirrors 251 and 252 such as fly back times is considered.

In the above-mentioned explanation, it is described that the RF frequency is switched to 1 MHz and is measured from 492 nm to 660 nm for every 4 nm, but It is needless to say that the RF frequency may be properly determined in consideration of the wavelength resolution of the AOTF 311, the entire time of data acquisition, and a necessary range of the spectrum and the pitch width etc. And, it is needless to say that the reason why the data is acquired by the wavelength band longer than 488 nm of the laser which is the excitation light in a wavelength band is that the fluorescence is generated by longer wavelength than 488 nm.

Excitation light of longer wavelength becomes overlapping with the fluorescence by the excitation light of shorter wavelength when measuring the double stained sample with two kinds of fluorescent dyes. Therefore, in this case, the spectrum data may be measured by excluding the RF frequency corresponding to the wavelength of the excitation light of longer wavelength. This is the reason the reflected light of the excitation beam has far higher intensity than that of fluorescent one.

In the laser scanning microscope according to the first embodiment as mentioned above, the AOTF 311 is arranged on a fluorescent optical path. The frequency of the high frequency voltage of the AOTF 311 is switched and set. As a result, the spectrum characteristic data of the fluorescence can be detected by detecting an optical amount of each wavelength via the AOTF 311.

Figure 6A:
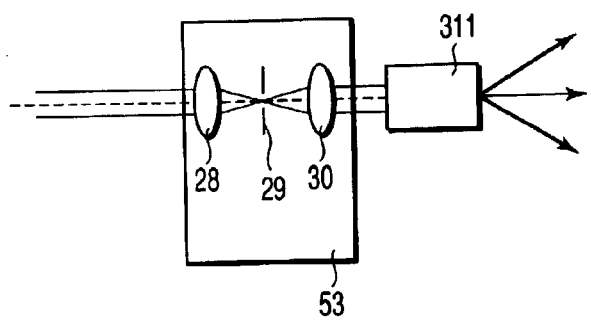
FIG. 6A and FIG. 6B are figures which show a modification of the confocal optical system.
Figure 6B:
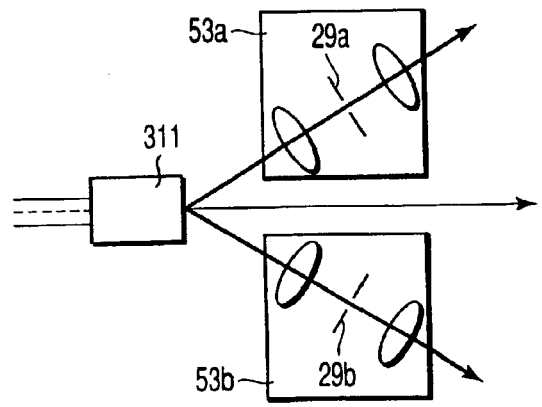
Figure 7:
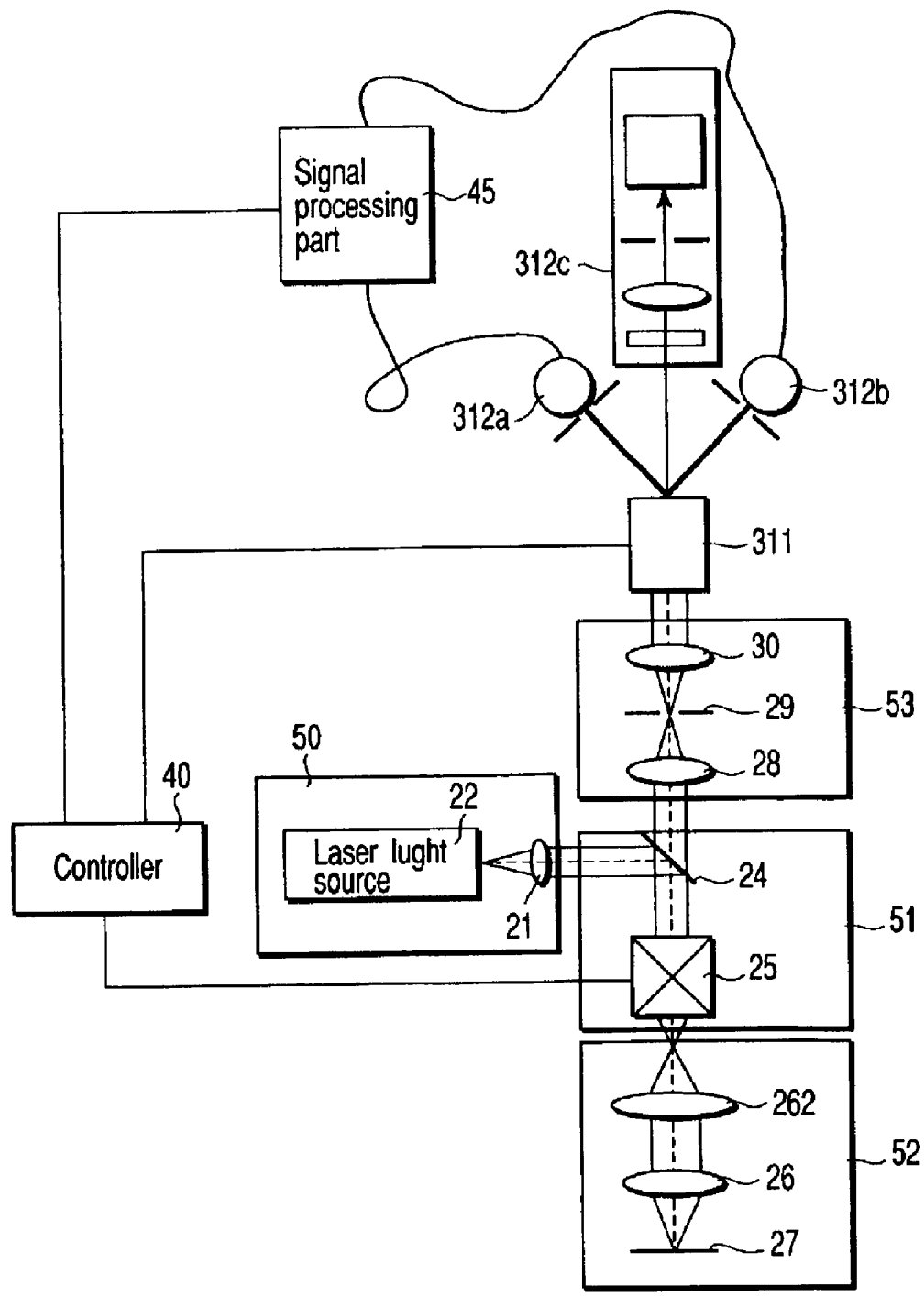
FIG. 7 is a figure which shows a schematic configuration of the laser scanning microscope according to the fourth embodiment.

Therefore, in the first embodiment, as described in FIG. 6A and FIG. 6B each of which is a conventional method of Japanese Patent Application KOKAI Publication No. 2000-56244, on a method of acquiring fluorescence spectrum, the complex structure, comprising optical dispersing means such as prism, focusing means for focusing the collected fluorescence spectrum series on the image position and a digital micro mirror (DMD) with electrically controllable tiny mirrors group for selecting of the detecting tiny spectrum range can be replaced with a single AOTF device. As a result, accurate spectrum data can be acquired at high speed by switching the RF frequency of an acousto-optic device with an easy configuration. And, the downsizing can be promoted. Moreover, an optical loss caused by the fiber transmission caused in the configuration to connect the spectrum part with the scanning device by the fiber for downsizing the scanning device can be suppressed as shown in FIG. 7 of Japanese Patent Application KOKAI Publication No. 2000-56244.

In addition, according to the first embodiment, since the data of the spectrum characteristics can be acquired at high speed because the switching speed of the RF frequency is 100 nsec to 1 $\mu$sec, high speed and accurate detection can be achieved.

The laser scanning microscope according to the first embodiment is configured that the acousto-optic device unit 31 detachably/attachably from/to the scanning unit 20. As a result, the part of the conventional laser scanning microscope can be made common between conventional fluorescence detection system and the first embodiment system which can selectively detect both of fluorescence light and the spectrum data. Accordingly, it is possible to upgrade the system easily.

U.S. Pat. No. 5,377,003 and U.S. Pat. No. 5,528,368 disclose a method of performing a fluorescent observation and the Raman spectrum with a two-dimensional detector like CCD by performing the illumination of black and white by using the AOTF or selecting the observation light by narrow bandwidth.

Typically, an internal distortion occurs in the prism when the frequency is applied to the prism ($TiO_2$ etc. are mainly used) having the birefingent, which is the main part of the AOTF. This internal distortion exerts the influence on the configuration which can perform two-dimensional detection similar to the CCD. The degradation is caused in the image to be observed which transmitted through the AOTF based on the internal distortion of prism to which the frequency is applied.

In the present invention, two-dimensional detection like CCD is not similarly performed but the surface of the sample is scanned in the following embodiments. The amount of the light which emitted from one point of the sample is detected, therefore, such an image degradation is not caused in the present invention.

(Second Embodiment)

Figure 3:
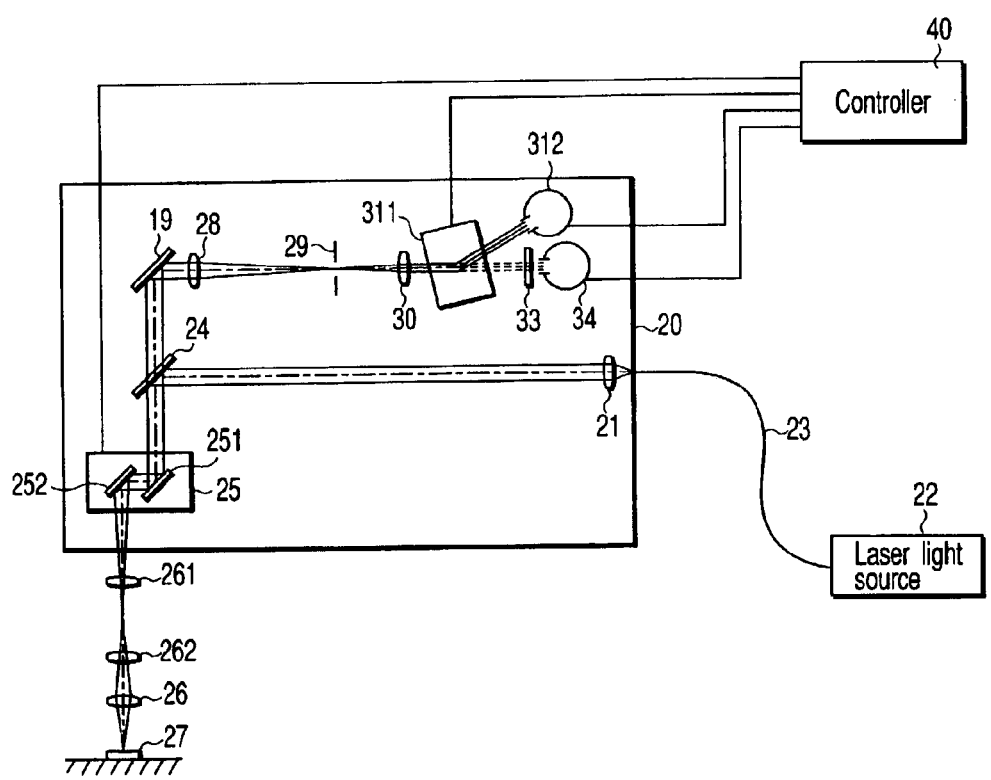
FIG. 3 is a figure which shows a main part configuration of the laser scanning microscope according to the second embodiment of present invention.

The second embodiment will be explained referring to FIG. 3. FIG. 3 is a figure which shows a schematic configuration of the laser scanning microscope according to the second embodiment. In FIG. 3, the same symbols are fixed as the same parts in FIG. 1, and the explanation thereof will be omitted.

In the second embodiment, the AOTF 311 also has the function as the optical path switching mirror 32 by arranging the AOTF 311 at the position where the optical path switching mirror 32 explained by FIG. 1.

In the above-mentioned configuration, it does not make AOTF 311 work, by not applying the RF frequency to that, to acquire a usual scanned image on the optical detector 34. As a result, all fluorescent wavelengths transmit the AOTF 311, are led to the optical detector 34 through barrier filter 33, and are detected.

And, when acquiring the spectrum characteristic data of the fluorescence, substantially similar to the first embodiment, the RF frequency of wavelength is applied to the AOTF 311. As a result, the fluorescent wavelength is deflected by the AOTF 311 as mentioned above, is led to the optical detector 312, and is detected.

It becomes possible to acquire the scanning image or the spectrum characteristic data by detecting light with the optical detector 34 without applying the RF frequency on the AOTF 311 at all or detecting it with the optical detector 312 applying the RF frequency according to the second embodiment. As a result, since the optical path switching mirror 32 can be saved compared with the first embodiment, the configuration can be more simplified.

The first and second above-mentioned embodiments may be modified as follows. For instance, the spectrum characteristic data is acquired by measuring the first-order diffracted light beam diffracted by the RF frequency with the optical detector 312 in the first and second embodiments, but a 0th-order diffracted light beam passing through the AOTF 311 may be detected with the optical detector. In this case, an optical amount that the wavelength of the fluorescence (diffracted as first-order diffraction light) corresponding to the RF frequency is subtracted from the sum total of an optical amount of the fluorescent wavelength transmitted through the barrier filter 33 will be detected for each RF frequency with the optical detector 312. The spectrum characteristic data can be obtained by performing reverse processing for these values. As mentioned above, it becomes possible to acquire highly accurate data since the fluorescent optical amount is much larger than when the first-order diffracted light beam is detected.

(Third Embodiment)

FIG. 4 is the figure which shows a schematic configuration of the laser scanning microscope according to the third embodiment of present invention. The laser scanning microscope in FIG. 4 has a light source part 50, a scanning optical system 51, a microscope 52, a confocal optical system 53, the AOTF 311, the detectors 312a and 312b, a control part 40, and a signal processing part 45. In FIG. 4, the same reference symbols are fixed to the same part as FIG. 1 or FIG. 2, and the detailed explanation will be omitted.

The point where the laser scanning microscope shown in FIG. 4 and that of FIG. 1 are different is the point that the detector 312a and 312b detect positive and negative first-order diffracted light beams by the AOTF 311. Therefore, a signal processing circuit 45 is newly provided.

The light from the light source part 50 is led to the microscope 52 through the scanning optical system 51 as excitation light by dichroic mirror 24, and excites the sample 27. The sample 27 labeled with a fluorescent reagent is excited by the excitation light. The fluorescence emitted from the sample 27 is separated as the fluorescence by dichroic mirror 24 through the microscope 52 and the scanning optical system 51. Next, the fluorescence arrives at the AOTF 311 by passing the confocal optical system 53. Though it is not shown in the figure, the specific driver for applying a specific frequency to the AOTF 311 to select the desired wavelength and the wavelength width is provided. The fluorescence is separated to the three optical paths of deflected positive and negative first-order diffracted light beams which have the wavelength component selected by the AOTF and functions as orthogonal polarized components with each other, and 0-th order diffracted light beam whose wavelength is not selected and which becomes an component of no deflection.

Each of the positive and negative first-order diffracted light beams is received by the detectors 312a and 312 (Hereafter, called as a "PMT"), an optical amount is detected, the signals from PMTs 312a and 312b are controlled in the signal processing part 45, and the data can be made as a sum signal and/or a difference signal.

As mentioned above, by providing the detectors to the optical paths of two fluorescences deflected in different directions or the reflected light, respectively, as a wavelength which corresponds to the frequency applied with the acousto-optic device, and treating those detection signals as a synthetic signal such as the sum signal and the difference signal, fluorescence of which the desired wavelength is selected or fluorescent intensity of the sum total of the reflected light, etc. can be efficiently acquired. The components which derive from the sample can be acquired from fluorescence or the reflected light to which the desired wavelength is selected if their signals are treated individually. These can be performed at high speed in an electric operation and can be switched easily.

Figure 5A:
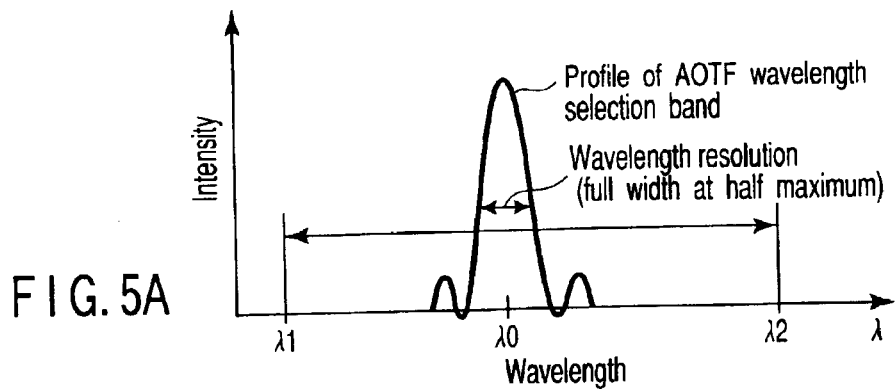
FIG. 5A and FIG. 5B are figures to explain an example of mimetically widening the bandwidth.
Figure 5B:
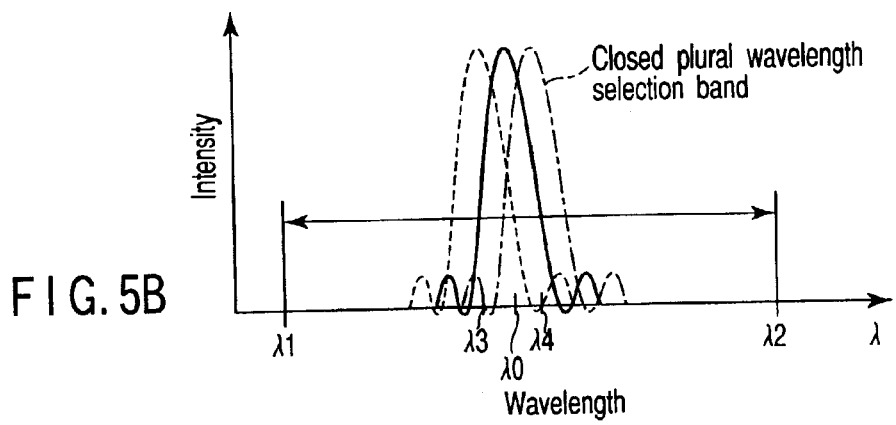

The operation of the AOTF 311 is performed as shown in FIG. 5A and FIG. 5B by combining with the driver not shown in the figure.

The first-order diffracted light beam which has the wavelength characteristics shown in FIG. 5A can be obtained from the AOTF 311 according to the applied frequency from the driver. The frequency from the driver is corresponding to the wavelength λ0, and a specific wavelength band is obtained as a spectrum because of the relationship of the diffraction efficiency on which this frequency and wavelength depend. And then, the wavelength resolution in the AOTF 311 can be determined. These usually differ depending on the incident beam characteristics to the AOTF such as the size, the field of view, the wavelength, and the polarized light to the AOTF. As the scanning confocal laser microscope is used here, just a fluorescence beam of parallel light beam may be treated, and comparative light resolution high several nm to several tens nm level can be obtained. According to an acousto-optic effect of the AOTF311, the positive and negative first-order diffracted light beams contain almost the same wavelength characteristics selected as mentioned above, furthermore, are separated to mutually orthogonal polarized two light components in each optical path of positive and negative paths, and are detected respectively. The effect of this polarized light separation is similar to a general polarized light beam splitter. It become possible to separate fluorescence which has a random polarized light to two polarized components with the same wavelength band, and set the selective wavelength freely.

In addition, lower bound value λ1 and upper limit λ2 are set to the wavelength as shown in FIG. 5A. It is possible to detect a spectrum by sweeping the frequency corresponding to the band, that is, by scanning the central wavelength. This operation can be performed at very high-speed and without mechanical vibration because of performing an electric operation without requiring the mechanical one at all. By combining with the scanning optical system 51 of this embodiment, it becomes easy to achieve acquisition of the image of two-dimension and/or three dimension, and hybrid detection of the spectrum acquisition at high speed.

Moreover, 0-th order diffracted light which becomes wavelength other than being selected passes birefringence index crystal in the AOTF 311, and is trapped by an optical stopper which prevents stray light. The component included in 0-th order diffracted light beam at this time is the fluorescent component other than the characteristics of the FIG. 5A to which wavelength is selected with the AOTF 311 out of the fluorescences emitted from the sample 27 and holds the polarized light characteristics of the fluorescence from the sample 27. At this time, a little optical amount loss by transmittance in the crystal occurs in 0-th order diffracted light beam. In general, the fluorescence has the wide wavelength spectrum compared with the wavelength resolution of the AOTF, in addition, is not explicitly shown in the FIG. 5A because there may be a case of using a plurality of fluorescent dyes.

An on/off of the specific wavelength selection on the AOTF 311 is easily achieved by an electric operation. As a result, the light can be separated according to the wavelength position and the band to be detected. In a word, the spectrum detection by the wavelength selection and the frequency sweep can be quickly performed in a state of cutting the laser completely so that the leakage light beam of the laser beam which functions as the excitation wavelength is not led to the detection, that is, the AOTF311 is electrically set (turned-off) not to become the active state at the wavelength position (frequency) of the laser. A plurality of the wavelength positions (frequency) are set to a plurality of lasers on the driver in electricity, and these can be achieved easily.

The further feature of the AOTF 311 is shown in FIG. 5B.

The AOTF 311 has the characteristics in which a plurality of independent frequencies are applied at the same time. FIG. 5B is a sample to obtain three wavelength bands of λ0, λ3, and λ4 by giving three kinds of frequencies. The wavelength resolution to one frequency of the AOTF 311 is fixed by the wavelength Full Width at Half Maximum (that is, high wavelength resolution) and cannot be varied fundamentally. Then, by bringing λ0, λ3, and λ4 close mutually, and concretely bringing the frequency applied to the AOTF 311 close, three spectra form envelope and the wavelength full width at half maximum can be expanded. Lower bound value λ1 and upper limit λ2 are set as mentioned above, and this envelope is also possible to be swept by the wavelength band. As a result, the wavelength width can be widely taken easily, and it is possible to correspond also to the sample which emits dark fluorescence. The number of frequencies which can be applied to is determined by combination of the characteristics of the AOTF 311 and the driver. It is not limited to the above-mentioned example and is also possible to apply more frequencies.

As mentioned above, two or more center wavelength can be selected by giving two or more frequencies to an acousto-optic device at the same time and wider width of the selective wavelength can be set than the comparatively narrow wavelength resolution obtained conventionally with the acousto-optic device by adjoining those center wavelength. In addition, efficient spectrum data can be acquired also with the sample of comparatively low level fluorescent intensity by sweeping in those center wavelength band where adjacent two or more center wavelengths are set. Thus, the method of giving a plurality of frequencies to an acousto-optic device at the same time and setting wider width of the selective wavelength can similarly apply not only this embodiment but also other embodiments also to the first and second embodiments and the following embodiments.

Fluorescence will be separated to positive and negative first-order diffracted light beams as a mutually orthogonal polarized component though it has almost the same wavelength characteristics. Though the first-order diffracted light beam will be detected by the PMTs 312a and 312b, at least two kinds of operation signals can be obtained by the signal processing part 45. If the signal from the PMTs 312a and 312b are output from the signal processing part 45 as a sum signal, it can be treated as a fluorescent sum total signal according to the set wavelength width. In addition, if the signals from the PMTs 312a and 312b are output as a difference signal or an independent signal through the signal processing part 45, it is possible to treat it as a fluorescent polarized light signal generated according to the state of an actual fluorescent reagent and the fluorescence polarized light analysis can be performed.

FIG. 6A and FIG. 6B are figures which show modification of the confocal optical system. FIG. 6A has a confocal optical system in the common optical path presented as one embodiment of the present invention. On the other hand, since various light beams are usually diffracted in the spectrum detection, in general, only desired positive and negative first-order diffracted light beams are detected as shown in FIG. 4 and the slit or a large-scale pinhole is frequently allocated before of detector 312a and 312b to prevent the stray light. The optical amount loss by vignetting occurs easily, too, in no small way when these confocal optical systems and two slits are put on the optical path. Then, to overlap the both functions and avoid the loss, of course, confocal optical system may be arranged in each optical system of optical paths of positive and negative first-order diffracted light beams diffracted as shown in FIG. 6B. As a result, though the complexity as apparatus increases, it is also possible to give two effects of a confocal effect and the stray light cutting.

In the third embodiment, by using the AOTF 311 to detect the spectrum, the laser scanning microscope with no mechanical drive, high effective spectrum, furthermore, high-speed and high-resolution evaluation spectrum can be achieved. In addition, the polarized light characteristics of the fluorescence can be detected. By detecting the positive and negative first-order diffracted light beams (fluorescent components) with the selected same wavelength component and orthogonal polarized light component respectively, it becomes possible to switch to usually the same fluorescent sum total signal and the fluorescent polarized light signal easily and make more detail quantative measurement of fluorescence the fluorescence which occurs by an actual sample.

Though there is respect which the device is comparatively enlarged in the conventional spectrum technique, in this embodiment, the detector can be comparatively made small by using the AOTF.

(Fourth Embodiment)

FIG. 7 is a figure which shows a schematic configuration of the laser scanning microscope according to the fourth embodiment of present invention.

The laser scanning microscope according to the fourth embodiment has a configuration which is almost similar to that of the third embodiment. The modification is given to the detector of the third embodiment in the fourth embodiment. That is, the third detection system 312c is provided as a main part of the laser scanning microscope.

The fluorescence is separated to positive and negative first-order diffracted light beams and 0-th order diffracted light beam in the AOTF 311. The positive and negative first-order diffracted light beams are as mentioned above, but the 0-th order diffracted light beam is a component transmitted through the AOTF311 and is not deflected, and has the component whose wavelength is not selected among the fluorescence from the sample 27. The third detection system is provided to this optical path and can be configured with the detector of a conventional filter type as one example. Concretely, the detector which has a barrier filter and a photomultiplier tube (PMT) which cuts the laser beam and extracts only the desired fluorescence for 0-th order diffracted light beam after passing the AOTF 311 may be provided and the confocal optical system may be configured with a confocal lens and a pinhole if necessary according to the degree of the stray light after AOTF 311. It is also possible that the third the detector 312c may be provided as a plurality of detectors as well as a conventional scanning confocal laser microscope.

That is, even if special apparatuses are not combined, the spectrum detection can be performed by detecting positive and negative first-order diffracted light beams using the AOTF 311, similar detection to the detection of wider wavelength range and the conventional one can be performed by using the filter, and it becomes to facilitate switching of both of them. As the detection using the filter, almost methods which can be executed with laser scanning microscope by the conventional filter detection may be used.

Though the detector of a conventional filter type which is not shown in the figure is given as an example as the third detector 312C, an external spectrum system, an avalanche photodiode (APD), a line sensor, and a multichannel sensor, etc. can be used by using the optical path of this 0-th order diffracted light beam, and it is needless to say that it is possible to be more multiplex by the use range of this optical path.

Therefore, the component which is not polarized by the optical path of a 0-th order diffracted light beam can be detected by the filter in addition to the spectrum detection by the AOTF 311, for instance, it is possible to obtain a hybrid laser scanning microscope in which the spectrum detection and the detection of the filter type can be easily switched. The switching of the spectrum detection and the detection of a conventional filter type are also easy. Moreover, it becomes possible to cover a wide use range by the purpose and use method, for example, such that it is possible to easily contribute also to the more optimal filter selection by the spectrum detection etc.

Thus, the fluorescence or the reflected light component whose wavelength is not selected can be detected and the apparatus is configured so as to be able to perform hybrid measurement by arranging it on the optical path of 0-th diffracted light beam to which the third detector is not deflected by the frequency in an acousto-optic device.

As mentioned above, it is possible to envelope by the selection of the desired center wavelength or the desired wavelength band of the center wavelength and efficiently acquire the desired fluorescence or the reflected light at high-speed and high accuracy as spectrum data, by detecting the fluorescence or the reflected light deflected to two different optical paths by the acousto-optic device with at least one detector and adjusting the frequency applied to the acousto-optic device. The system has the broad general purpose regardless of this comparatively simple configuration, is configured in the small space, and can be downsized.

(Fifth Embodiment)

Figure 8:
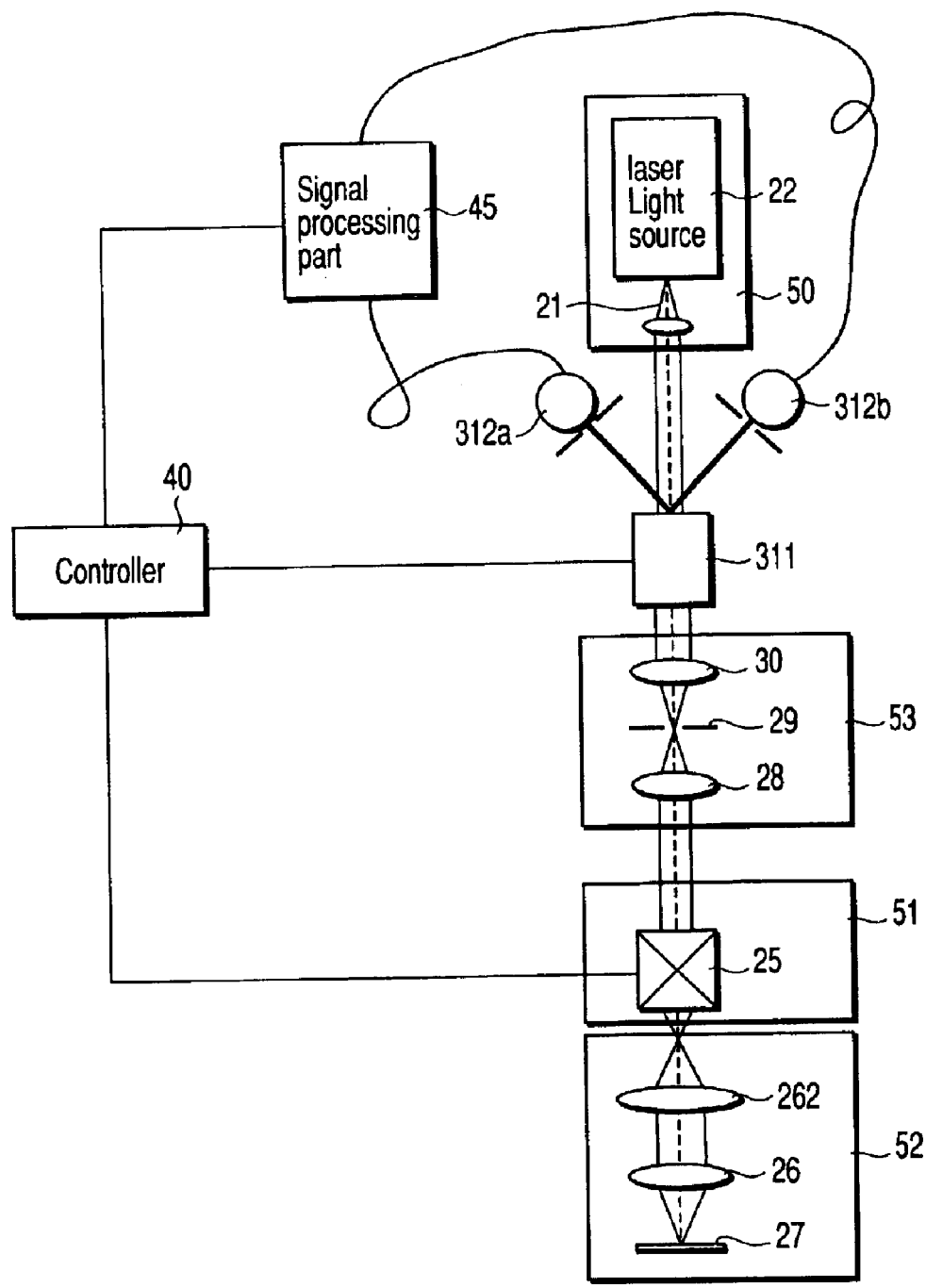
FIG. 8 is a figure which shows a schematic configuration of the laser scanning microscope according to the fifth embodiment.

FIG. 8 is a figure which shows a schematic configuration of the laser scanning microscope according to the fifth embodiment of present invention.

The main part of the laser scanning microscope comprises a light source part 50 having a laser light source 22 and a collimator lens 21, a scanning optical part 51 of which has a galvanometer mirror 6 which scans on XY plane two-dimensionally, a microscope 52 having a tube lens 8 and an objective 9, a confocal optical system part 14 including a pinhole 13, an AOTF 311 which is an acousto-optic device, detectors 312a and 312b configured with two photomultiplier tubes (PMT) which are detectors, and a signal processing part 45 where the signals of the detectors 312a and 312b are controlled. Here, the introduction of the laser beam from the laser light source part 50 may be performed through the optical fiber, of course as well as the first embodiment. FIG. 8 shows a basic configuration of the system. The multi line laser may be adopted to provide a plurality of the wavelengths as the laser light source 22, and a plurality of single line laser light sources may be configured together.

A device achieving other equal effects except PMT, which can detect the signal by performing photoelectron conversion, may be used as a detector.

The function and the effect of the fifth embodiment are almost similar to the third embodiment, but differ therefrom in the point explained as follows.

The laser beam from the light source part 50 passes the AOTF311 and the confocal optical system 53, is led to the microscope 52 as excitation light through the scanning optical system 51, and excites the sample 27. At this time, the confocal optical system 53 carries out the role as one spatial filter for the excitation light. The sample 27 labeled by a fluorescent reagent is excited by the excitation light. As a result, the emitted fluorescence passes the scanning optical system 51 and the confocal optical system 53 through the microscope 10 again and arrives at the AOTF 311. At this time, the confocal optical system functions to achieve a confocal effect for the fluorescence. Though it is not shown in the AOTF 311, a peculiar driver, which applies a specific frequency to the AOTF 311 in order to select the desired wavelength and the wavelength width, is prepared thereto. The fluorescence emitted from the sample is separated to the positive and negative first-order diffracted light beams which have wavelength components which is selected by the AOTF 311 and become mutually orthogonal polarized components.

That is, the ATOF 15 has a function as the beam splitter which separates the excitation light which is the laser beam on the optical path 0-th order diffracted light beam and the positive and negative first-order diffracted light beams in which the fluorescence emitted from the sample 27 is selected in wavelength and deflected. The excitation light from the laser light source 23 is incident to the AOTF 311 from an opposite direction to the original traveling direction on optical path of a 0-th order diffracted light beam of the AOTF 311. There are some drawbacks in the current coating technology such that the wavelength characteristics of the dielectric substance film coated to a conventional dichroic mirror does not have a so steep standing up curve, the maximum transmittance around 85% (little low), and difficulties of the multiband to make up to three excitation wavelengths, etc. The loss of an optical amount occurs basically only in the transmittance of the crystal in the AOTF 311 since the AOTF 311 works as a prism for the excitation light in the fifth embodiment. If the direction of the polarized light from the laser light source 23 is rotated and matched to the polarized direction of birefringence index crystal to obtain the higher efficiency, the loss thereof can be more reduced. At this time, by introducing the laser beam into the AOTF 311 using the polarized light preserving optical fiber, the agreement of the direction of the polarized light can be easily achieved by only rotating the direction of the fiber.

Therefore, easy and high effective cut-off to a plurality of excitation wavelength can be easily performed by not activating the AOTF 311 of the spectrum detection in electricity at those wavelength positions, without adding to the system great and switching at all. If the wavelength selection of the positive and negative first-order diffracted light beams can be performed with the high wavelength resolution, which is peculiar to the AOTF311, and can be turned off as mentioned above in the position neighborhood of the excitation wavelength, the fluorescence can be separated and acquired with very high efficiency which cannot be obtained in conventional one. Of course, considering in view of respect of the use efficiency of light, the confocal optical system 53 may be arranged as shown in FIG. 6B. By providing two functions of the beam splitter and the spectrum detection to the AOTF 311 as mentioned above, the system can be configured with the very simple configuration, and can be downsized.

The fluorescent components included in the optical path of the 0-th order diffracted light beam with no deflection can be separated by using the dichroic mirror before the laser light source and it is also possible to provide the detector of a conventional filter type and to perform hybrid measurement. It is needless to say that the action and the function can be obtained as same as the third embodiment and the fourth embodiment by using the AOTF 311.

As mentioned above, by providing two functions of the beam splitter and the spectrum function to the AOTF 311, it is possible to highly effectively separate the excitation light/fluorescence, to achieve the spectrum detection with high speed and the high resolution as a function of the AOTF 311, and to downsize the entire system. Furthermore, since it becomes possible to inspect the characteristics of the fluorescent polarized light, which derives from the fluorescent reagent and the sample, by using the polarized light characteristics of positive and negative first-order diffracted light beams, thereby it is possible to perform the hybrid measurement with small sized system.

Thus, the laser beam from the laser light source can be incident from opposite to the traveling direction of the 0-th order diffracted light beam originally passing the acousto-optic device, and the laser beam can be illuminated to the sample through the scanning optical system and the microscope without being influenced from the frequency applied to an acousto-optic device. Therefore, the acousto-optic device can be functioned as a role of the above-mentioned beam splitter with higher use efficiency of light. In this case, the frequency applied to an acousto-optic device only may not match up with the known wavelength of the laser to be merely illuminated to the sample, and the advantage that the separation of the excitation light and the fluorescence with high S/N which cannot be achieved by a conventional dichroic mirror can be achieved and it is possible to set up also two or more wavelength of the laser very easily, too.

The fluorescence or the reflected light which derives from the state and the condition of the sample can be acquired as the polarized component by deflecting the positive and negative first-order diffracted light beams which are mutually orthogonal polarized components from the acousto-optic device in two different directions and detecting each of them with at least one detector, in addition to the acquisition of efficient spectrum data which uses the above-mentioned acousto-optic device.

Therefore, the present invention can be executed in various modes within the scope of the present invention without being limited to each of the above-mentioned embodiments. For instance, though the spectrum characteristic data is acquired by measuring the first-order diffracted light beam (s) with the optical detector 312 diffracted by the RF frequency in this embodiment, the 0-th order diffracted light beam, which passes the AOTF 311 may be detected with the optical detector 34. In this case, an optical amount of which an optical amount of the wavelength of the fluorescence (is diffracted as the first order diffraction light corresponding to the RF frequency is subtracted from the sum total of the fluorescent wavelength which is transmitted through the barrier filter 33 is detected with the optical detector 312 for each RF frequency. The spectrum characteristic data can be obtained by reverse-processing of these values. With this configuration, it becomes possible to acquire highly accurate data, since the fluorescent optical amount is much larger than when the first-order diffracted light beam is detected. In addition, the present invention of various stages is included in each above-mentioned embodiment. Various inventions can be extracted by appropriate combinations of the plurality of configurations of components which are disclosed herein.

For instance, even if the several configurations are deleted from all configurations shown in the embodiments, in a case that the problem described in the subject to be solved by the present invention can be solved and the effect described in the advantages of the present invention can be achieved, the configuration of which this configuration is deleted can be extracted as an invention.

In the above-mentioned third to fifth embodiments, if the laser beam which uses the optical fiber as a light source as described above is introduced, the avoidance of heat and vibration, good quality point light source, and the downsizing of the scanning optical system and the detection system can be achieved as well-known in general.

A desired plurality of excitation wavelengths may be combined as a light source by using the laser generating the multi line and a combiner, which synthesizes the beams using a plurality of lasers. It is also possible to provide the second AOTF thereto, and to provide the functions of the laser selection and the intensity adjustment.

Though it is not shown in the figure, by leading the positive and negative first-order diffracted light beams to one detector with a mirror etc. and providing the shutter to each optical path, the positive first-order diffracted light beam and the negative first-order diffracted light beam may be detected at the same time and may be alternately detected while switching. If both shutters are opened at the same time, the sum total signal of the fluorescence can be detected. Two different fluorescent polarized elements can be detected by electrically synchronizing the switching of the shutter and the timing of the detector and separating the signals.

Especially, though it does not describe clearly in detail when the reflected light is detected, as one example, the present invention can be applied also to the Raman spectrum method such that the scattering is caused in the laser beam illuminated to the sample 27 and the wavelength characteristics of the scattered light is inspected according to the physical properties.

In this case, though the wavelength of the laser beam and the scattered light are extremely adjacent, especially, the Raman scattering can be efficiently detected by the configuration of the fifth embodiment with high wavelength resolution by the AOTF 311. Thus, it is needless to say it is not limited to the spectrum detection of the fluorescence but to be able to apply the present invention widely as a general spectrometer.

Though the present invention is described as the scanning confocal laser microscope and the excitation light from the laser light source 23 scans on the sample surface 11 along the X-Y plane through the scanning optical system 7, the same advantage and the effect can be achieved by using the AOTF 311 even in a basic configuration of which the excitation light is illuminated only to certain one point. In this case, other scanning means which drives the stage as scanning means and other scanning means which is not scanned along the X-Y plane to obtain the desired data and the image acquisition.

The laser scanning microscope according to the first aspect of the present invention is characterized by comprising: an objective focusing a laser beam on a sample, and takes fluorescence or reflected light from the sample; optical scanning means for scanning the laser beam on the sample two-dimensionally; an acousto-optic device, arranged on an optical path of a fluorescence or a reflected light, which selects and deflects only a light beam with the wavelength which corresponds to incident fluorescence or the reflected light and a frequency of the applied high frequency voltage; optical detection means for detecting a light beam through the acousto-optic device; and frequency scanning means for switching and setting a frequency of a high frequency voltage applied to the acousto-optic device.

Desirable modes of the laser scanning microscope according to the first aspect are as follows. The following each modes can be applied by properly and combining independently respectively.

(1) A beam splitter, which separates the laser beam from the fluorescence or the reflected light, is further provided, and the beam splitter is arranged between the objective and the acousto-optic device.

(2) Light detected by the optical detection means is a first-order diffracted light beam deflected by the acousto-optic device.

(3) A second detector which detects a 0-th order light transmitted through the acousto-optic device is further provided.

(4) The frequency scanning means switches and sets the frequency of the high frequency voltage by synchronizing with scanning of the optical scanning means to detect a spectrum characteristics for each pixel.

(5) The acousto-optic device and the optical detection means are configured as one unit and is set insertable and detachable to the detection optical path separated by the beam splitter.

(6) A scanning range by the frequency scanning means does not include a frequency of the high frequency voltage corresponding to the wavelength of the laser beam.

(7) The acousto-optics device deflects the fluorescence or the reflected light to different directions of a first optical path and a second optical path, and the detector includes at least one detector arranged on the first optical path and the second optical path, respectively.

(8) A detector which detects a 0-th order light transmitted through the acousto-optic device is further provided.

(9) The acousto-optic device deflects the fluorescence or the reflected light to the first and second optical paths in different directions, and the laser beam is incident from a third optical path other than the first second optical path and the second optical path.

(10) The fluorescence or the reflected light on the first optical path and the second optical path deflected by the acousto-optic device is a positive and negative first-order diffraction light beams which are mutually orthogonal polarized light components.

(11) A signal processing part configured to process signals from two detectors provided to the deflected first and second optical paths as a synthetic signal which becomes a sum signal or a difference signal or as an independent signal, respectively is further provided.

(12) The acousto-optics device can set a plurality of center wavelengths or frequencies, and a spectrum formed with each of the plurality of center wavelengths or the frequencies can be partially overlapped by closing the plurality of center wavelengths or the frequencies or being adjacent thereto with each other to be able to select a wider wavelength width.

(13) The acousto-optic device deflects the fluorescence or the reflected light in a first optical path and a second optical path of mutually different directions, and the deflection device which leads the fluorescence or the reflected light led to the first optical path and the second optical path to one detector is provided.

(14) Shutters provided to the first optical path and the second optical path respectively are further provided.

(15) The third optical path is an optical path of a 0-th order diffracted light beam which is not deflected by the frequency of the acousto-optic device. (16) The laser beam on the third optical path is on the optical path of a 0-th order diffracted light beam output from the acousto-optic device and traveling direction thereof is opposite to the 0-th order diffracted light beam.

The laser scanning microscope according to the second aspect of the present invention is characterized by comprising: an objective focusing a laser beam on a sample, and takes fluorescence or reflected light from the sample; optical scanning means for scanning the laser beam on the sample two-dimensionally; an acousto-optic device arranged on the optical path of the fluorescence or the reflected light, the acousto-optic device diffracted the light of wavelength corresponding to the frequency of the high frequency voltage as + first-order diffracted light beam and − first-order diffracted light beam out of the incident fluorescence or reflected light, when the high frequency voltage is applied, and passing the incident fluorescence or reflected light as 0-th order diffracted light beam when said high frequency voltage is not applied to; a high frequency signal control part configured to control on and off of the application of the high frequency voltage to the acousto-optic device and set the high frequency voltage; a first optical detector configured to receive the + first-order diffracted light beam; and a second optical detector configured to receive the − first-order diffracted light beam.

Desirable modes of the laser scanning microscope according to the second aspect are as follows. The following each modes can be applied by properly and combining independently respectively.

(1) Means for generating an image of the sample based on the value of which the output signal of the first optical detector and the output signal of the second optical detector are added is further provided.

(2) Spectrum data of the fluorescence or the reflected light is acquired by enveloping the frequency of the high frequency voltage by the high frequency signal control part and acquiring the output signal of the first and the second optical detector in each frequency.

(3) In (2), a third optical detector to receive the 0-th order diffracted light beam is further provided, and an image of the sample is generated by using the output signal of the third optical detector when the high frequency voltage is not applied to the acousto-optic device.

The laser scanning microscope according to the third aspect of the present invention is characterized by comprising: an objective focusing a laser beam on a sample, and takes fluorescence or reflected light from the sample; optical scanning means for scanning the laser beam on the sample two-dimensionally; an acousto-optic device arranged on the optical path of the fluorescence or the reflected light, the acousto-optic device diffracted the light of wavelength corresponding to the frequency of the high frequency voltage as + first-order diffracted light beam and − first-order diffracted light beam out of the incident fluorescence or reflected light, when the high frequency voltage is applied, and passing the incident fluorescence or reflected light as 0-th order diffracted light beam when said high frequency voltage is not applied to; a high frequency signal control part configured to control on and off of the application of the high frequency voltage to the acousto-optic device and set the high frequency voltage; a first optical detector configured to receive the + first-order diffracted light beam; and a second optical detector configured to receive the − first-order diffracted light beam, and the laser light source is arranged on optical path of a 0-th order diffracted light beam so that the laser beam transmitted through the acousto-optic device without modulating and is led to the objective.

The laser scanning microscope according to the fourth aspect of the present invention is characterized by comprising: an objective focusing a laser beam on a sample, and takes fluorescence or reflected light from the sample; optical scanning means for scanning the laser beam on the sample two-dimensionally; an acousto-optic device arranged on the optical path of the fluorescence or the reflected light, the acousto-optic device diffracted the light of wavelength corresponding to the frequency of the high frequency voltage as first-order diffracted light beam out of the incident fluorescence or reflected light, when the high frequency voltage is applied, and passing the incident fluorescence or reflected light as 0-th order diffracted light beam when said high frequency voltage is not applied to; a high frequency signal control part configured to control on and off of the application of the high frequency voltage to the acousto-optic device and set the high frequency voltage; and a light detector to receive the first-order diffracted light beam, and spectrum data of the fluorescence or the reflected light is acquired by enveloping the frequency of the high frequency voltage by the high frequency signal control part and acquiring the output signal of the first and the second optical detector in each frequency.

In the fourth aspect, it is preferable to further comprise a second optical detector to receive the 0-th order diffracted light beam, and an image of the sample is generated by using the output signal of the second optical detector when the high frequency voltage is not applied to the acousto-optic device.

As described above in detail, according to the present invention, the laser scanning microscope which can promote the downsizing, and achieve the detection of accurate spectrum characteristic data with simple configuration.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A laser scanning microscope comprising:
   an objective for focusing a laser beam on a sample, and for transmitting light from the sample;
   optical scanning means for two-dimensionally scanning the laser beam on the sample;
   an acousto-optic device which is arranged on a detection optical path of the light from the sample and which selectably deflects only light with a wavelength corresponding to a frequency of an applied high frequency voltage;
   an optical detector for detecting light from the acousto-optic device;
   frequency scanning means for switching and setting a frequency of the applied high frequency voltage; and
   a beam splitter which is arranged between the objective and the acousto-optic device to divide an optical path of the laser beam from the detection optical path of the light from the sample;
   wherein the light detected by the optical detector is a first-order diffracted light beam deflected by the acousto-optic device; and wherein the frequency scanning means switches and sets the frequency of the high frequency voltage by synchronizing with the scanning of the optical scanning means to detect spectrum characteristic data for each pixel.

2. The laser scanning microscope according to claim 1, wherein the acousto-optic device and the optical detector are configured as one unit which is insertable to and removable from the detection optical path.

3. The laser scanning microscope according to claim 2, wherein a range scanned by the frequency scanning means does not include a frequency of the high frequency voltage corresponding to a wavelength of the laser beam.

4. The laser scanning microscope according to claim 1, wherein a range scanned by the frequency scanning means does not include a frequency of the high frequency voltage corresponding to a wavelength of the laser beam.

5. A laser scanning microscope comprising:
an objective for focusing a laser beam on a sample, and for transmitting light from the sample;
optical scanning means for two-dimensionally scanning the laser beam on the sample;
an acousto-optic device which is arranged on a detection optical path of the light from the sample, and which selectably deflects only light with a wavelength corresponding to a frequency of an applied high frequency voltage;
an optical detector for detecting light from the acousto-optic device;
frequency scanning means for switching and setting a frequency of the applied high frequency voltage; and
a beam splitter which is arranged between the objective and the acousto-optic device to divide an optical path of the laser beam from the detection optical path of the light from the sample;
wherein the light, detected by the optical detector is a first-order diffracted, light beam deflected by the acousto-optic device; and
wherein the acousto-optic device and the optical detector are configured as one unit which is insertable to and removable from the detection optical path.

6. The laser scanning microscope according to claim 5, wherein a range scanned by the frequency scanning means does not include a frequency of the high frequency voltage corresponding to a wavelength of the laser beam.

7. A laser scanning microscope comprising:
an objective for focusing a laser beam on a sample, and for transmitting light from the sample;
optical scanning means for two-dimensionally scanning the laser beam on the sample;
an acousto-optic device which is arranged on a detection optical path of the light from the sample, and which selectably deflects only light with a wavelength corresponding to a frequency of an applied high frequency voltage;
an optical detector for detecting light from the acousto-optic device;
frequency scanning means for switching and setting a frequency of the applied high frequency voltage; and
a beam splitter which is arranged between the objective and the acousto-optic device to divide an optical path of the laser beam from the detection optical path of the light from the sample;
wherein the light detected by the optical detector is a first-order diffracted light beam deflected by the acousto-optic device; and wherein a range scanned by the frequency scanning means does not include a frequency of the high frequency voltage corresponding to a wavelength of the laser beam.

8. A laser scanning microscope comprising:
an objective for focusing a laser beam on a sample, and for transmitting light from the sample;
optical scanning means for two-dimensionally scanning the laser beam on the sample;
an acousto-optic device which is arranged on a detection optical path of the light from the sample, and which selectably deflects only light with a wavelength corresponding to a frequency of an applied high frequency voltage;
an optical detector for detecting light from the acousto-optic device;
frequency scanning means for switching and setting a frequency of the applied high frequency voltage; and
a beam splitter which is arranged between the objective and the acousto-optic device to divide an optical path of the laser beam from the detection optical path of the light from the sample;
wherein the light detected by the optical detector is a first-order diffracted light beam deflected by the acousto-optic device; and
wherein frequencies corresponding to a plurality of center wavelengths are settable in the acousto-optic device, and
wherein spectra formed with each of the plurality of center wavelengths are adapted to be partially overlapped by bringing the plurality of center wavelengths or frequencies close together to select a wider wavelength width.

9. A laser scanning microscope comprising:
an objective for focusing a laser beam on a sample, and for transmitting light from the sample;
optical scanning means for two-dimensionally scanning the laser beam on the sample;
an acousto-optic device which is arranged on a detection optical path of the light from the sample, and which selectably deflects only light with a wavelength corresponding to a frequency of an applied high frequency voltage;
an optical detector for detecting light from the acousto-optic device;
frequency scanning means for switching and setting a frequency of the applied high frequency voltage; and
a beam splitter which is arranged between the objective and the acousto-optic device to divide an optical path of the laser beam from the detection optical path of the light from the sample;
wherein the frequency scanning means switches and sets the frequency of the high frequency voltage by synchronizing with the scanning of the optical scanning means to detect spectrum characteristic data for each pixel.

10. The laser scanning microscope according to claim 9, wherein the acousto-optic device and the optical detector are configured as one unit which is insertable to and removable from the detection optical path.

11. The laser scanning microscope according to claim 10, wherein a range scanned by the frequency scanning means does not include a frequency of the high frequency voltage corresponding to a wavelength of the laser beam.

12. The laser scanning microscope according to claim 9, wherein a range scanned by the frequency scanning means does not include a frequency of the high frequency voltage corresponding to a wavelength of the laser beam.

13. A laser scanning microscope comprising:
an objective for focusing a laser beam on a sample, and for transmitting light from the sample;
optical scanning means for two-dimensionally scanning the laser beam on the sample;
an acousto-optic device which is arranged on a detection optical path of the light from the sample, and which selectably deflects only light with a wavelength corresponding to a frequency of an applied high frequency voltage;
an optical detector for detecting light from the acousto-optic device;
frequency scanning means for switching and setting a frequency of the applied high frequency voltage; and
a beam splitter which is arranged between the objective and the acousto-optic to divide an optical path of the laser beam from the detection optical path off the light from the sample;
wherein the acousto-optic device and the optical detector are configured as one unit which is insertable to and removable from the detection optical path.

14. The laser scanning microscope according to claim 13, wherein a range scanned by the frequency scanning means does not include a frequency of the high frequency voltage corresponding to a wavelength of the laser beam.

15. A laser scanning microscope comprising:
an objective for focusing a laser beam on a sample, and for transmitting light from the sample;
optical scanning means for two-dimensionally scanning the laser beam on the sample;
an acousto-optic device which is arranged on a detection optical path of the light from the sample, and which selectably deflects only light with a wavelength corresponding to a frequency of an applied high frequency voltage;
an optical detector for detecting light from the acousto-optic device;
frequency scanning means for switching and setting a frequency of the applied high frequency voltage; and
a beam splitter which is arranged between the objective and the acousto-optic device to divide an optical path of the laser beam from the detecting optical path of the light from the sample;
wherein a range scanned by the frequency scanning means does not include a frequency of the high frequency voltage corresponding to a wavelength of the laser beam.

16. A laser scanning microscope comprising:
an objective for focusing a laser beam on a sample, and for transmitting light from the sample;
optical scanning means for two-dimensionally scanning the laser beam on the sample;
an acousto-optic device which is arranged on a detection optical path of the light from the sample, and which selectably deflects only light with a wavelength corresponding to a frequency of an applied high frequency voltage;
an optical detector for detecting light from the acousto-optic device;
frequency scanning means for switching and setting a frequency of the applied high frequency voltage; and
a beam splitter which is arranged between the objective and the acousto-optic device to divide an optical path of the laser beam from the detection optical path of the light from the sample;
wherein the acousto-optic device deflects the light from the sample as a first light beam along a first optical path and a second light beam in a different direction along a second optical path, and
wherein the optical detector comprises a first detector arranged on the first optical path, and a second optical detector is arranged on the second optical path.

17. The laser scanning microscope according to claim 16, further comprising an additional optical detector which detects a 0-th order light transmitted through the acousto-optic device.

18. The laser scanning microscope according to claim 16, wherein the laser beam is incident from a third optical path different from the first optical path and the second optical path.

19. The laser scanning microscope according to claim 16, wherein the first and second light beams deflected by the acousto-optic device are respectively positive and negative first-order diffracted light beams which are mutually orthogonal polarized light components.

20. The laser scanning microscope according to claim 19, further comprising a deflection device which leads the first light beam and the second light beam to one of the first detector and the second detector.

21. The laser scanning microscope according to claim 20, further comprising shutters in each of the first optical path and the second optical path.

22. The laser scanning microscope according to claim 19, further comprising a signal processing part configured to process signals from the first detector and the second detector as a synthetic signal which is one of a sum signal and a difference signal or as respective independent signals.

23. The laser scanning microscope according to claim 19, wherein frequencies corresponding to a plurality of center wavelengths are settable in the acousto-optic device, and
wherein spectra formed with each of the plurality of center wavelengths are adapted to be partially overlapped by bringing the plurality of center wavelengths or frequencies close together to select a wider wavelength width.

24. The laser scanning microscope according to claim 16, further comprising a signal processing part configured to process signals from the first detector and the second detector as a synthetic signal which is one of a sum signal or a difference signal and as respective independent signals.

25. The laser scanning microscope according to claim 16, wherein frequencies corresponding to a plurality of center wavelengths are settable in the acousto-optic device, and
wherein spectra formed with each of the plurality of center wavelengths are adapted to be partially overlapped by bringing the plurality of center wavelengths or frequencies close together to select a wider wavelength width.

26. A laser scanning microscope comprising:
an objective for focusing a laser beam on a sample, and for transmitting light from the sample;
optical scanning means for two-dimensionally scanning the laser beam on the sample;
an acousto-optic device which is arranged on a detection optical path of the light from the sample, and which selectably deflects only light with a wavelength corresponding to a frequency of an applied high frequency voltage;

an optical detector for detecting light from the acousto-optic device;

frequency scanning means for switching and setting a frequency of the applied high frequency voltage; and a beam splitter which is arranged between the objective and the acousto-optic device to divide an optical path of the laser beam from the detection optical path of the light from the sample;

wherein the acousto-optics device deflects the light from the sample as a first light beam along a first optical path and a second light beam in a different direction along a second optical path, and wherein light that is not deflected to the first and second optical paths travels along a third optical path.

27. The laser scanning microscope according to claim 26, wherein the first and second light beams deflected by the acousto-optic device are respectively positive and negative first-order diffracted light beams which are mutually orthogonal polarized light components.

28. The laser scanning microscope according to claim 27, further comprising a deflection device which leads the first light beam and the second light beam to one of the first detector and the second detector.

29. The laser scanning microscope according to claim 28, further comprising shutters in each of the first optical path and the second optical path.

30. The laser scanning microscope according to claim 27, wherein the optical detector comprises a first optical detector provided in the first optical path, and a second optical detector is provided in the second optical path; and wherein the laser scanning microscope further comprises a signal processing part configured to process signals from the first detector and the second detector as a synthetic signal which is one of a sum signal and a difference signal or as respective independent signals.

31. The laser scanning microscope according to claim 27, wherein frequencies corresponding to a plurality of center wavelengths are settable in the acousto-optic device, and wherein spectra formed with each of the plurality of center wavelengths are adapted to be partially overlapped by bringing the plurality of center wavelengths or frequencies close together to select a wider wavelength width.

32. The laser scanning microscope according to claim 26, wherein the optical detector comprises a first optical detector provided in the first optical path, and a second optical detector is provided in the second optical path; and wherein the laser scanning microscope further comprises a signal processing part configured to process signals from the first detector and the second detector as a synthetic signal which is one of a sum signal and a difference signal or as respective independent signals.

33. The laser scanning microscope according to claim 26, wherein frequencies corresponding to a plurality of center wavelengths are settable in the acousto-optic device, and wherein spectra formed with each of the plurality of center wavelengths are adapted to be partially overlapped by bringing the plurality of center wavelengths or frequencies close together to select a wider wavelength width.

34. The laser scanning microscope according to claim 26, wherein the light that travels along the third optical path is a 0-th order diffracted light beam which is no deflected by the frequency of the acousto-optic device.

35. A laser scanning microscope comprising:

an objective for focusing a laser beam on a sample, and for transmitting light from the sample;

optical scanning means for two-dimensionally scanning the laser beam on the sample;

an acousto-optic device which is arranged on a detection optical path of the light from the sample, and which selectably deflects only light with a wavelength corresponding to a frequency of an applied high frequency voltage;

a first optical detector for detecting light deflected by the acousto-optic device;

a second detector which detects a 0-th order diffracted light beam transmitted through the acousto-optic device;

frequency scanning means for switching and setting a frequency of the applied high frequency voltage; and a beam splitter which is arranged between the objective and the acousto-optic device to divide an optical path of the laser beam from the detection optical path of the light from the sample;

wherein the light detected by the first optical detector is a first-order diffracted light beam deflected by the acousto-optic device.

36. The laser scanning microscope according to claim 35, wherein the frequency scanning means switches and sets the frequency of the high frequency voltage by synchronizing with the scanning of the optical scanning means to detect spectrum characteristic data for each pixel.

37. The laser scanning microscope according to claim 36, wherein the acousto-optic device and at least the first optical detector are configured as one unit which is insertable to and removable from the detection optical path.

38. The laser scanning microscope according to claim 37, wherein a range scanned by the frequency scanning means does not include a frequency of the high frequency voltage corresponding to a wavelength of the laser beam.

39. The laser scanning microscope according to claim 36, wherein a range scanned by the frequency scanning means does not include a frequency of the high frequency voltage corresponding to a wavelength of the laser beam.

40. The laser scanning microscope according to claim 35, wherein the acousto-optic device and at least the first optical detector are configured as one unit which is insertable to and removable from the detection optical path.

41. The laser scanning microscope according to claim 40, wherein a range scanned by the frequency scanning means does not include a frequency of the high frequency voltage corresponding to a wavelength of the laser beam.

42. The laser scanning microscope according to claim 35, wherein a range scanned by the frequency scanning means does not include a frequency of the high frequency voltage corresponding to a wavelength of the laser beam.

43. A laser scanning microscope comprising:

an objective for focusing a laser beam on a sample, and for transmitting light from the sample;

optical scanning means for two-dimensionally scanning the laser beam on the sample;

an acousto-optic device which is arranged on a detection optical path of the light from the sample and which selectably deflects only light with a wavelength corresponding to a frequency of an applied high frequency voltage;

an optical detector for detecting light from the acousto-optic device;

frequency scanning means for switching and setting a frequency of the applied high frequency voltage; and a beam splitter which is arranged between the objective and the acousto-optic device to divide an optical path of the laser beam from the detection optical path of the light from the sample;

wherein frequencies corresponding to a plurality of center wavelengths are settable in the acousto-optic device, and wherein spectra formed with each of the plurality of center wavelengths are adapted to be partially overlapped by bringing the plurality of center wavelengths or frequencies close together to select a wider wavelength width.

44. A laser scanning microscope comprising:

an objective for focusing a laser beam on a sample, and for transmitting light from the sample;

optical scanning means for two-dimensionally scanning the laser beam on the sample;

an acousto-optic device which is arranged on a detection optical path of the light from the sample, and which selectably deflects only light with a wavelength corresponding to a frequency of an applied high frequency voltage;

an optical detector for detecting light from the acousto-optic device; and frequency scanning means for switching and setting a frequency of the applied high frequency voltage;

wherein the light detected by the optical detector is a first-order diffracted light beam deflected by the acousto-optic device; and wherein the frequency scanning means switches and sets the frequency of the high frequency voltage by synchronizing with the scanning of the optical scanning means to detect spectrum characteristic data for each pixel.

45. The laser scanning microscope according to claim 44, wherein the acousto-optic device and the optical detector are configured as one unit which is insertable to and removable from the detection optical path.

46. The laser scanning microscope according to claim 45, wherein a range scanned by the frequency scanning means does not include a frequency of the high frequency voltage corresponding to a wavelength of the laser beam.

47. The laser scanning microscope according to claim 44, wherein a range scanned by the frequency scanning means does not include a frequency of the high frequency voltage corresponding to a wavelength of the laser beam.

48. A laser scanning microscope comprising:

an objective for focusing a laser beam on a sample, and for transmitting light from the sample;

optical scanning means for two-dimensionally scanning the laser beam on the sample;

an acousto-optic device which is arranged on a detection optical path of the light from the sample, and which selectably deflects only light with a wavelength corresponding to a frequency of an applied high frequency voltage;

an optical detector for detecting light from the acousto-optic device; and frequency scanning means for switching and setting a frequency of the applied high frequency voltage;

wherein the light detected by the optical detector is a first-order diffracted light beam deflected by the acousto-optic device; and wherein the acousto-optic device and the optical detector are configured as one unit which is insertable to and removable from the detection optical path.

49. The laser scanning microscope according to claim 48, wherein a range scanned by the frequency scanning means does not include a frequency of the high frequency voltage corresponding to a wavelength of the laser beam.

50. A laser scanning microscope comprising:

an objective for focusing a laser beam on a sample, and for transmitting light from the sample;

optical scanning means for two-dimensionally scanning the laser beam on the sample;

an acousto-optic device which is arranged on a detection optical path of the light from the sample, and which selectably deflects only light with a wavelength corresponding to a frequency of an applied high frequency voltage;

an optical detector for detecting light from the acousto-optic device; and frequency scanning means for switching and setting a frequency of the applied high frequency voltage;

wherein the light detected by the optical detector is a first-order diffracted light beam deflected by the acousto-optic device; and wherein a range scanned by the frequency scanning means does not include a frequency of the high frequency voltage corresponding to a wavelength of the laser beam.

51. A laser scanning microscope comprising:

an objective for focusing a laser beam on a sample, and for transmitting light from the sample;

optical scanning means for two-dimensionally scanning the laser beam on the sample;

an acousto-optic device which is arranged on a detection optical path of the light from the sample, and which selectably deflects only light with a wavelength corresponding to a frequency of an applied high frequency voltage;

an optical detector for detecting light from the acousto-optic device, and frequency scanning means for switching and setting a frequency of the applied high frequency voltage;

wherein the light detected by the a optical detector is a first-order diffracted light beam deflected by the acousto-optic device; and wherein frequencies corresponding to a plurality of center wavelengths are settable in the acousto-optic device; and wherein spectra formed with each of the plurality of center wavelengths are adapted to be partially overlapped by bringing the plurality of center wavelengths or frequencies close together to select a wider wavelength width.

52. A laser scanning microscope comprising:

an objective for focusing a laser beam on a sample, and for transmitting light from the sample;

optical scanning means for two-dimensionally scanning the laser beam on the sample;

an acousto-optic device which is arranged on a detection optical path of the light from the sample, and which selectably deflects only light with a wavelength corresponding to a frequency of an applied high frequency voltage;

an optical detector for detecting light from the acousto-optic device; and frequency scanning means for switching and setting a frequency of the applied high frequency voltage;

wherein the frequency scanning means switches and sets the frequency of the high frequency voltage by synchronizing with the scanning of the optical scanning means to detect spectrum characteristic data for each pixel.

53. The laser scanning microscope according to claim 52, wherein the acousto-optic device and the optical detector are configured as one unit which is insertable to and removable from the detection optical path.

54. The laser scanning microscope according to claim 53, wherein a range scanned by the frequency scanning means does not include a frequency of the high frequency voltage corresponding to a wavelength of the laser beam.

55. The laser scanning microscope according to claim 52, wherein a range scanned by the frequency scanning means does not include a frequency of the high frequency voltage corresponding to a wavelength of the laser beam.

56. A laser scanning microscope comprising:
an objective for focusing a laser beam on a sample, and for transmitting light from the sample;
optical scanning means for two-dimensionally scanning the laser beam on the sample;
an acousto-optic device which is arranged on a detection optical path of the light from the sample and which selectably deflects only light with a wavelength corresponding to a frequency of an applied high frequency voltage;
an optical detector for detecting light from the acousto-optic device; and
frequency scanning means for switching and setting a frequency of the applied high frequency voltage;
wherein a range scanned by the frequency scanning means does not include a frequency of the high frequency voltage corresponding to a wavelength of the laser beam.

57. A laser scanning microscope comprising:
an objective for focusing a laser beam on a sample, and for transmitting light from sample;
optical scanning means for two-dimensionally scanning the laser beam on the sample;
an acousto-optic device which is arranged on a detection optical path of the light from the sample, and which selectably deflects only light with a wavelength corresponding to a frequency of an applied high frequency voltage;
an optical detector for detecting light from the acousto-optic device; and
frequency scanning means for switching and setting a frequency of the applied high frequency voltage;
wherein the acousto-optic device deflects the light from the sample as a first light beam along a first optical path and a second light beam in a different direction along a second optical path;
wherein the optic detector comprises a first detector arranged on the first optical path, and a second optical detector is arranged on the second optical path; and
wherein the laser beam is incident from a third optical path different from the first optical path and the second optical path.

58. A laser scanning microscope comprising:
an objective for focusing a laser beam on a sample, and for transmitting light from the sample;
optical scanning means for two-dimensionally scanning the laser beam on the sample;
an acousto-optic device which is arranged on a detection optical path of the light from the sample, and which selectably deflects only light with a wavelength corresponding to a frequency of an applied high frequency voltage;
an optical detector for detecting light from the acousto-optic device; and
frequency scanning means for switching and setting a frequency of the applied high frequency voltage;
wherein the acousto-optic device deflects the light from the sample as a first light beam along a first optical path and a second light beam in a different direction along a second optical path;
wherein the optical detector comprises a first detector arranged on the first optical path, and a second optical detector is arranged on the second optical path; and
wherein the first and second light beams deflected by the acousto-optic device are respectively positive and negative first-order diffracted light beams which are mutually orthogonal polarized light components.

59. The laser scanning microscope according to claim 58, further comprising a deflection device which leads the first light beam and the second light beam to one of the first detector and the second detector.

60. The laser scanning microscope according to claim 59, further comprising shutters in each of the first optical path and the second optical path.

61. The laser scanning microscope according to claim 58, further comprising a signal processing part configured to process signals from the first detector and the second detector as a synthetic signal which is one of a sum signal and a difference signal or as respective independent signals.

62. The laser scanning microscope according to claim 58, wherein frequencies corresponding to a plurality of center wavelengths are settable in the acousto-optic device, and
wherein spectra formed with each of the plurality of center wavelengths are adapted to be partially overlapped by bringing the plurality of center wavelengths or frequencies close together to select a wider wavelength width.

63. A laser scanning microscope comprising:
an objective for focusing a laser beam on a sample, and for transmitting light from the sample;
optical scanning means for two-dimensionally scanning the laser beam on the sample;
an acousto-optic device which is arranged on a detection optical path of the light from the sample, and which selectably deflects only light with a wavelength corresponding to a frequency of an applied high frequency voltage;
an optical detector for detecting light from the acousto-optic device; and
frequency scanning means for switching and setting a frequency of the applied high frequency voltage;
wherein the acousto-optic device deflects the light from the sample as a first light beam along a first optical path and a second light beam in a different direction along a second optical path;
wherein the optical detector comprises a first detector arranged on the first optical path, and a second optical detector is arranged on the second optical path; and
wherein a signal processing part is provided which is configured to process signals from the first detector and the second detector as a synthetic signal which is one of a sum signal and a difference signal or as respective independent signals.

64. A laser scanning microscope, comprising:
an objective for focusing a laser beam on a sample, and for transmitting light from the sample;
optical scanning means for two-dimensionally scanning the laser beam on the sample;
an acousto-optic device which is arranged on a detection optical path of the light from the sample, and which selectably deflects only light with a wavelength corresponding to a frequency of an applied high frequency voltage;
an optical detector for detecting light from the acousto-optic device; and
frequency scanning means for switching and setting a frequency of the applied high frequency voltage;
wherein the acousto-optic device deflects the light from the sample as a first light beam along a first optical path and a second light beam in a different direction along a second optical path;
wherein the optical detector comprises a first detector arranged on the first optical path, and a second optical detector is arranged on the second optical path;
wherein frequencies corresponding to a plurality of center wavelengths are settable in the acousto-optic device, and
wherein spectra formed with each of the plurality of center wavelengths are adapted to be partially overlapped by bringing the plurality of center wavelengths or frequencies close together to select a wider wavelength width.

65. A laser scanning microscope comprising:
an objective for focusing a laser beam on a sample, and for transmitting light from the sample;
optical scanning means for two-dimensionally scanning the laser beam on the sample;
an acousto-optic device which is arranged on a detection optical path of the light from the sample, and which selectably deflects only light with a wavelength corresponding to a frequency of an applied high frequency voltage;
an optical detector for detecting light from the acousto-optic device; and
frequency scanning means for switching and setting a frequency of the applied high frequency voltage;
wherein the acousto-optics device deflects the light from the sample as a first light beam along a first optical path and a second light beam in a different direction along a second optical path, and wherein light that is not deflected to the first and second optical paths travels along a third optical path.

66. laser scanning microscope according to claim 65, wherein the first and second light beams deflected by the acousto-optic device are respectively positive and negative first-order diffracted light beams which are mutually orthogonal polarized light components.

67. The laser scanning microscope according to claim 66, further comprising a deflection device which leads the first light beam and the second light beam to one of the first detector and the second detector.

68. The laser scanning microscope according to claim 67, further comprising shutters in each of the first optical path and the second optical path.

69. The laser scanning microscope according to claim 66, further comprising a signal processing part configured to process signals from two detectors provided to the deflected first an second optical paths as a synthetic signal which is one of a sum signal and a difference signal or as respective independent signals.

70. The laser scanning microscope according to claim 66, wherein frequencies corresponding to a plurality of center wavelengths are settable in the acousto-optic device, and
wherein spectra formed with each of the plurality of center wavelengths are adapted to be partially overlapped bringing the plurality of center wavelengths or frequencies close together to select a wider wavelength width.

71. The laser scanning microscope according to claim 65, further comprising a signal processing part configured to process signals from two detectors provided to the deflected first and second optical paths as a synthetic signal which is one of a sum signal and a difference signal or as respective independent signals.

72. The laser scanning microscope according to claim 65, wherein frequencies corresponding to a plurality of center wavelengths are settable in the acousto-optic device, and
wherein spectra formed with each of the plurality of center wavelengths are adapted to be partially overlapped by bringing the plurality of center wavelengths or frequencies close together to select a wider wavelength width.

73. The laser scanning microscope according to claim 65, wherein the light that travels along the third optical path is a 0-th order diffracted light beam which is not deflected by the frequency of the acousto-optic device.

74. A laser scanning microscope comprising:
an objective for focusing a laser beam on a sample, and for transmitting light from the sample;
optical scanning means for two-dimensionally scanning the laser beam on the sample;
an acousto-optic device which is arranged on a detection optical path of the light from the sample, and which selectably deflects only light with a wavelength corresponding to a frequency of an applied high frequency voltage;
an optical detector for detecting light from the acousto-optic device; and
frequency scanning means for switching and setting a frequency of the applied high frequency voltage;
wherein the acousto-optic device deflects the light from the sample to first and second optical paths in different directions, and the laser beam is incident from a third optical path which is different from the first optical path and the second optical path.

75. The laser scanning microscope according to claim 74, wherein light from the sample deflected to the first optical path and the light from the sample deflected to the second optical path are respectively positive and negative first-order diffraction light beams which are mutually orthogonal polarized light components.

76. The laser scanning microscope according to claim 75, further comprising a deflection device which leads the first light beam and the second light beam to one of the first detector and the second detector.

77. The laser scanning microscope according to claim 76, further comprising shutters in each of the first optical path and the second optical path.

78. The laser scanning microscope according to claim 75, further comprising a signal processing part configured to process signals from two detectors provided to the deflected first an second optical paths as a synthetic signal which is one of a sum signal and a difference signal or as respective independent signals.

79. The laser scanning microscope according to claim 75, wherein frequencies corresponding to a plurality of center wavelengths are settable in the acousto-optic device, and wherein spectra formed with each of the plurality of center wavelengths are adapted to be partially overlapped by bringing the plurality of center wavelengths or frequencies close together to select a wider wavelength width.

80. The laser scanning microscope according to claim 74, further comprising a signal processing part configured to process signals from two detectors provided to the deflected first and second optical paths as a synthetic signal which is one of a sum signal and a difference signal or as respective independent signals.

81. The laser scanning microscope according to claim 74, wherein frequencies corresponding to a plurality of center wavelengths are settable in the acousto-optic device, and wherein spectra formed with each of the plurality of center wavelengths are adapted to be partially overlapped by bringing the plurality of center wavelengths or frequencies close together to select a wider wavelength width.

82. The laser scanning microscope according to claim 74, wherein the third optical path includes an optical path of a 0-th order diffracted light beam which is not deflected by the frequency of the acousto-optic device.

83. The laser scanning microscope according to claim 74, wherein the laser beam on the third optical path travels along the optical path of a 0-th order diffracted light beam output from the acousto-optic device, and the laser beam travels in a direction opposite to a traveling direction of the 0-th order diffracted light beam.

84. A laser scanning microscope comprising:

an objective for focusing a laser beam on a sample, and for transmitting light from the sample;

optical scanning means for two-dimensionally scanning the laser beam on the sample;

an acousto-optic device which is arranged on a detection optical path of the light from the sample, and which selectably deflects only light with a wavelength corresponding to a frequency of an applied high frequency voltage;

an optical detector for detecting light from the acousto-optic device; and frequency scanning means for switching and setting a frequency of the applied high frequency voltage;

wherein frequencies corresponding to a plurality of center wavelengths are settable in the acousto-optic device, and wherein spectra formed with each of the plurality of center wavelengths are adapted to be partially overlapped by bringing the plurality of center wavelengths or frequencies close together to select a wider wavelength width.

85. A laser scanning microscope comprising:

an objective for focusing a laser beam on a sample, and for transmitting light from the sample;

optical scanning means for two-dimensionally scanning the laser beam on the sample;

an acousto-optic device arranged on the optical path of the light from the sample, wherein when a high frequency voltage is applied the acousto-optic device diffracts part of the light from the sample having a wavelength co responding to a frequency of the high frequency voltage as a positive first-order diffracted light beam and a negative first-order diffracted light beam and when the high frequency voltage is not applied the acousto-optic device passes incident light from the sample as a 0-th order diffracted light beam;

a high frequency signal control part configured to control turning on and off of the application of the high frequency voltage to the acousto-optic device and setting of the high frequency voltage;

a first optical detector to receive the positive first-order diffracted light beam; and a second optical detector to receive the negative first-order diffracted light beam.

86. The laser scanning microscope according to claim 85, further comprising means for generating an image of the sample based on a sum of an output signal of the first optical detector and an output signal of the second optical detector.

87. The laser scanning microscope according to claim 85, wherein spectrum data of the light from the sample is acquired by enveloping the frequency of the high frequency voltage by the high frequency signal control part an acquiring an output signal of the first and the second optical detector in each frequency.

88. The laser scanning microscope according to claim 87, further comprising a third optical detector to receive the 0-th order diffracted light beam, wherein an image of the sample is generated using an output signal of the third optical detector when the high frequency voltage is not applied to the acousto-optic device.

89. A laser scanning microscope comprising:

an objective for focusing a laser beam on a sample, and for transmitting light from the sample;

optical scanning means for two-dimensionally scanning the laser beam on the sample;

an acousto-optic device arranged on the optical path of the light from the sample, wherein when a high frequency voltage is applied the acousto-optic device diffracts a part of the light from the sample having a wavelength corresponding to a frequency of the high frequency voltage as a positive first-order diffracted light beam, and a negative first-order diffracted light beam and when the high frequency voltage is not applied the acousto-optic device passes incident light from the sample as a 0-th order diffracted light beam;

a high frequency signal control part configured to control turning on and off of the application of the high frequency voltage to the acousto-optic device and setting of the high frequency voltage;

a first optical detector to receive the positive first-order diffracted light beam; and a second optical detector to receive the negative first-order diffracted light beams;

wherein a laser light source is arranged on an optical path of the 0-th order diffracted light beam such that the laser beam is transmitted through the acousto-optic device without modulating and is led to the objective.

90. A laser scanning microscope comprising:

an objective for focusing a laser beam on a sample, and for transmitting light from the sample;

optical scanning means for two-dimensionally scanning the laser beam on the sample; an acousto-optic device arranged on the optical path of the light from the sample, wherein when a high frequency voltage is applied the acousto-optic device diffracts a part of the light from the sample having a wavelength c responding to a frequency of the high frequency voltage as a first-order diffracted light beam and when the high frequency voltage is n t applied the acousto-optic device passes incident light from the sample as a 0-th order diffracted light beam a high frequency signal control part configured to control turning on and off of he application of the high frequency voltage to the acousto-optic device and setting of the high frequency voltage; and a light detector o receive the first-order diffracted light beam;

wherein spectrum data of the light from the sample s acquired by enveloping the frequency of the high frequency voltage by the high frequency signal control part and acquiring an output signal of the first and the second optical detector in each frequency.

91. The laser scanning microscope according to claim 90, further comprising a second optical detector to receive the 0-th order diffracted light beam, wherein an image of the sample is generated using the an output signal of the second optical detector when the high frequency voltage is applied to the acousto-optic device.

* * * * *